(12) United States Patent
Huang et al.

(10) Patent No.: US 11,123,353 B2
(45) Date of Patent: Sep. 21, 2021

(54) USES OF ERGOSTEROL COMBINED WITH GEFITINIB, PREPARATION METHODS OF LIPOSOME AND FREEZE-DRIED POWDER THEREOF

(71) Applicant: Zhejiang Chinese Medical University, ZheJiang (CN)

(72) Inventors: Shengwu Huang, ZheJiang (CN); Ting Huang, ZheJiang (CN); Meijia Wu, ZheJiang (CN)

(73) Assignee: Zhejiang Chinese Medical University, Zhejiang (CN)

( * ) Notice: Subject to any disclaimer, the term of this patent is extended or adjusted under 35 U.S.C. 154(b) by 94 days.

(21) Appl. No.: 16/700,408

(22) Filed: Dec. 2, 2019

(65) Prior Publication Data
US 2021/0046090 A1 Feb. 18, 2021

(30) Foreign Application Priority Data

Aug. 12, 2019 (CN) .......................... 201910737667.2
Aug. 12, 2019 (CN) .......................... 201910737671.9
Aug. 12, 2019 (CN) .......................... 201910737672.3

(51) Int. Cl.
| | |
|---|---|
| *A61K 31/575* | (2006.01) |
| *A61K 31/5377* | (2006.01) |
| *A61K 9/127* | (2006.01) |
| *A61P 35/00* | (2006.01) |
| *A61K 47/10* | (2017.01) |
| *A61K 47/26* | (2006.01) |
| *A61K 9/16* | (2006.01) |

(52) U.S. Cl.
CPC .......... *A61K 31/575* (2013.01); *A61K 9/1277* (2013.01); *A61K 9/1682* (2013.01); *A61K 31/5377* (2013.01); *A61K 47/10* (2013.01); *A61K 47/26* (2013.01); *A61P 35/00* (2018.01)

(58) Field of Classification Search
None
See application file for complete search history.

(56) References Cited

U.S. PATENT DOCUMENTS

2006/0172014 A1* 8/2006 Curd .................... A61K 45/06
424/649

FOREIGN PATENT DOCUMENTS

| CN | 105663159 A | * | 6/2016 | ............. A61K 33/24 |
|---|---|---|---|---|
| CN | 105769878 A | * | 7/2016 | ........... A61K 31/575 |
| CN | 105816479 A | * | 8/2016 | ............. A61K 33/24 |

OTHER PUBLICATIONS

Bray, Freddie et al., Global Cancer Statistics 2018: GLOBOCAN Estimates of Incidence and Mortality Worldwide for 36 Cancers in 185 Countries, CA Cancer Journal for Clinicians 2018, pp. 394-424.

* cited by examiner

*Primary Examiner* — Brian J Davis
(74) *Attorney, Agent, or Firm* — Olive Law Group, PLLC

(57) ABSTRACT

The present disclosure relates to a drug combination for treating non-small cell lung cancer, in particular to uses of ergosterol combined with gefitinib, and belongs to the technical field of biomedicine. In the present disclosure, the mechanism of action that ergosterol (ERG) combined with gefitinib (GEF) induces apoptosis of non-small cell lung cancer (NSCLC) cells is firstly studied; then an RGG cyclic peptide/R8 peptide modified ERG combined with GEF active drug-loaded targeted liposome delivery system (RGD/R8-ERG/GEF-LIP) is constructed; and the RGD/R8-ERG/GEF-LIP is prepared into a freeze-dried powder to improve stability, quality evaluation and preliminary evaluation of in vitro anti-lung cancer effects are conducted, and a nude mouse lung cancer xenograft model is established for conducting preliminary pharmacodynamic research and in vivo targeting research.

13 Claims, 38 Drawing Sheets

Tab.1-1 Inhibitory rates of A549 cells at different time points in two single drug groups and combined drug group ($\bar{x} \pm s$)

| Group | Drug concentration (μM) | Inhibitory rate (%) 24 h | 48 h | 72 h |
|---|---|---|---|---|
| Control | / | 0.00 | 0.00 | 0.00 |
| ERG group | 5 | 41.24±1.74 | 48.06±1.40 | 50.09±1.58 |
|  | 10 | 49.26±5.94 | 54.24±3.08 | 53.82±2.62 |
|  | 20 | 50.74±6.58 | 57.44±0.61 | 61.87±0.40 |
|  | 40 | 57.67±4.76 | 61.12±0.09 | 64.87±2.66 |
|  | 80 | 60.29±0.56 | 67.56±6.46 | 71.12±3.22 |
|  | 160 | 66.84±4.87 | 72.77±4.67 | 79.59±2.57 |
| GEF group | 5 | 7.85±1.82 | 16.18±1.05 | 20.99±2.48 |
|  | 10 | 9.93±1.01 | 22.93±2.49 | 43.64±3.63 |
|  | 20 | 16.78±5.28 | 29.08±5.93 | 58.53±4.17 |
|  | 40 | 22.40±0.97 | 47.03±0.33 | 67.77±4.26 |
|  | 80 | 34.63±3.21 | 62.10±4.49 | 74.00±2.18 |
|  | 160 | 51.76±5.27 | 64.55±0.82 | 68.22±0.78 |
| ERG+GEF group | 5+5 | 66.67±1.15 | 73.27±0.85 | 74.46±2.48 |
|  | 10+10 | 75.03±0.96 | 77.28±0.93 | 78.24±3.63 |
|  | 20+20 | 76.63±1.72 | 80.83±1.03 | 81.33±4.17 |
|  | 40+40 | 77.42±2.48 | 82.14±0.49 | 84.66±4.26 |
|  | 80+80 | 80.19±1.15 | 82.43±0.45 | 85.56±2.18 |
|  | 160+160 | 81.19±1.37 | 82.73±0.66 | 86.86±0.78 |

Fig. 1

IC50 value of two single drug groups at different time points

| | ERG IC$_{50}$ (μM) | GEF IC$_{50}$ (μM) |
|---|---|---|
| 24 h | 15.05 | 144.33 |
| 48 h | 6.60 | 55.42 |
| 72 h | 5.88 | 25.47 |

Fig.2

Q value of synergistic inhibitory effect of ERG and GEF on A549 cells

| Group | Drug concentration (μM) | Treatment time (h) | | |
|---|---|---|---|---|
| | | 24 h | 48 h | 72 h |
| ERG+GEF group | 5+5 | 1.45 | 1.27 | 1.23 |
| | 10+10 | 1.38 | 1.19 | 1.06 |
| | 20+20 | 1.30 | 1.16 | 0.97 |
| | 40+40 | 1.15 | 1.03 | 0.95 |
| | 80+80 | 1.06 | 0.94 | 0.93 |
| | 160+160 | 0.97 | 0.92 | 0.89 |

Fig.3

Inhibitory rate of PC-9 cells at different time points in two single-drug groups and combination group ($\bar{x} \pm s$)

| Group | Drug concentration (μM) | Inhibitory rate (%) | | |
|---|---|---|---|---|
| | | 24 h | 48 h | 72 h |
| Control | / | 0.00 | 0.00 | 0.00 |
| ERG group | 5 | 18.82±2.16 | 26.42±1.64 | 39.50±0.50 |
| | 10 | 26.03±2.08 | 31.11±4.03 | 44.58±2.57 |
| | 20 | 30.20±1.39 | 34.16±2.78 | 49.21±2.12 |
| | 40 | 32.75±0.37 | 36.37±1.32 | 51.56±1.90 |
| | 80 | 46.49±0.82 | 47.40±1.70 | 54.38±0.65 |
| | 160 | 50.97±0.78 | 53.47±1.28 | 58.88±0.76 |
| | 320 | 54.43±1.56 | 61.42±0.80 | 69.05±0.58 |
| GEF group | 0.625 | 33.41±1.42 | 37.96±4.56 | 52.58±1.81 |
| | 1.25 | 36.97±3.63 | 45.22±2.60 | 53.62±4.01 |
| | 2.5 | 43.55±3.78 | 48.06±2.26 | 56.20±2.09 |
| | 5 | 45.26±3.25 | 50.40±1.87 | 61.20±2.71 |
| | 10 | 48.37±2.15 | 54.00±1.20 | 70.80±1.37 |
| | 20 | 51.09±2.40 | 69.89±2.23 | 80.20±1.73 |
| | 40 | 55.34±2.19 | 82.83±1.43 | 86.37±1.03 |
| GEF+ERG group | 0.625+5 | 65.76±2.16 | 71.81±1.64 | 82.29±0.50 |
| | 1.25+10 | 68.32±2.08 | 73.92±4.03 | 82.99±2.57 |
| | 2.5+20 | 70.87±1.39 | 76.62±2.78 | 83.68±2.12 |
| | 5+40 | 73.27±0.37 | 79.37±1.32 | 84.42±1.90 |
| | 10+80 | 74.08±0.82 | 80.20±1.70 | 87.05±0.65 |
| | 20+160 | 74.44±0.78 | 84.05±1.28 | 90.75±0.76 |
| | 40+320 | 79.12±1.56 | 84.89±0.80 | 91.07±0.58 |

Fig. 4

IC50 value of two single drug groups at different time points

|  | ERG IC50 (μM) | GEF IC50 (μM) |
|---|---|---|
| 24 h | 165.44 | 13.74 |
| 48 h | 110.82 | 2.82 |
| 72 h | 27.00 | 0.88 |

Fig. 5

Q value of synergistic inhibitory effect of ERG and GEF on PC-9 cells

| Group | Drug concentration (μM) | Treatment time (h) | | |
|---|---|---|---|---|
| | | 24 h | 48 h | 72 h |
| GEF +ERG group | 0.625+5 | 1.43 | 1.32 | 1.15 |
| | 1.25+10 | 1.28 | 1.19 | 1.12 |
| | 2.5+20 | 1.17 | 1.16 | 1.08 |
| | 5+40 | 1.16 | 1.16 | 1.04 |
| | 10+80 | 1.02 | 1.06 | 1.00 |
| | 20+160 | 0.98 | 0.98 | 0.99 |
| | 40+320 | 0.99 | 0.91 | 0.95 |

Fig. 6

Apoptotic rate of A549 cells induced by ERG and GEF ($\bar{x} \pm s$)

| Group | Drug concentration | Apoptotic rate (%) |
|---|---|---|
| Control | — | 5.64±0.25 |
| ERG | 10 μM | 6.64±0.54^ΔΔ |
| | 20 μM | 8.13±0.75** |
| | 40 μM | 10.12±0.37** |
| GEF | 10 μM | 9.53±0.45^ΔΔ |
| | 20 μM | 10.73±0.38 |
| | 40 μM | 14.23±0.64** |
| ERG+GEF | 10+10 μM | 10.96±0.53 |
| | 20+20 μM | 13.11±1.87 |
| | 40+40 μM | 16.31±0.28 |

Fig. 7

Apoptotic rate of PC-9 cells induced by ERG and GEF ($\bar{x} \pm s$)

| Group | Drug concentration | Apoptotic rate (%) |
|---|---|---|
| Control | — | 5.43±0.50 |
| ERG | 20 μM | 8.11±1.62^ΔΔ |
| | 40 μM | 10.46±1.29** |
| | 80 μM | 11.71±1.48** |
| GEF | 2.5 μM | 16.45±1.01 |
| | 5 μM | 18.14±0.68** |
| | 10 μM | 19.19±1.17** |
| ERG+GEF | 20+2.5 μM | 18.68±1.22 |
| | 40+5 μM | 21.33±1.47 |
| | 80+10 μM | 26.29±0.91 |

Fig. 8

Cell cycle distribution of A549 cells induced by ERG and GEF ($\bar{x} \pm s$)

| Group | Cell cycle (%) | | |
|---|---|---|---|
| | G0/G1 phase | S phase | G2/M |
| Control | 56.65±0.13 | 29.63±2.15 | 13.72±2.13 |
| ERG (20 μM) | 58.97±0.94* | 32.05±2.27* | 8.98±1.55* |
| GEF (20 μM) | 72.60±0.81** | 22.57±1.70** | 4.83±1.19** |
| ERG+GEF (20+20 μM) | 65.16±1.55* | 26.10±1.11 | 8.74±0.92** |

Fig. 9

Cell cycle distribution of PC-9 cells induced by ERG and GEF ($\bar{x} \pm s$)

| Group | Cell cycle (%) | | |
|---|---|---|---|
| | G0/G1 phase | S phase | G2/M |
| Control | 71.23±0.44 | 19.13±1.20 | 9.64±1.25 |
| ERG (40 μM) | 59.49±0.22** | 26.93±2.02** | 13.58±1.80** |
| GEF (5 μM) | 78.35±1.58** | 15.13±3.03 | 6.51±1.48* |
| ERG+GEF (40+5 μM) | 78.91±1.86** | 13.18±3.16* | 7.91±1.51 |

Fig. 10

Model formula

| Model | Model equation |
|---|---|
| Zero-order model | $Y=kt+k_1$ |
| First-order model | $Ln(1-Y)=-kt+k_1$ |
| Higuchi model | $Y=kt^{1/2}+k_1$ |

Fig. 11

Fitting results and correlation coefficients of cumulative drug release rate

| Model | Drugs | Fitting equation | $R^2$ |
|---|---|---|---|
| Zero-order model | GEF drug substance (pH 7.4) | $Y=0.2255t+0.2039$ | 0.9656 |
|  | GEF drug substance (pH 6.4) | $Y=0.0559t+0.5753$ | 0.8059 |
|  | ERG/GEF-LIP (pH 7.4) | $Y=0.1577t+0.0393$ | 0.9670 |
|  | ERG/GEF-LIP (pH 6.4) | $Y=0.1882t+0.0897$ | 0.9321 |
| First-order model | GEF drug substance (pH 7.4) | $Y=-0.4251t-0.1706$ | 0.9952 |
|  | GEF drug substance (pH 6.4) | $Y=-0.2947t-0.7647$ | 0.9660 |
|  | ERG/GEF-LIP (pH 7.4) | $Y=-0.2605t+0.0149$ | 0.9947 |
|  | ERG/GEF-LIP (pH 6.4) | $Y=-0.3929t+0.0096$ | 0.9912 |
| Higuchi model | GEF drug substance (pH 7.4) | $Y=0.4505t+0.0025$ | 0.9982 |
|  | GEF drug substance (pH 6.4) | $Y=4.5858x-1.8883$ | 0.9185 |
|  | ERG/GEF-LIP (pH 7.4) | $Y=0.4108t-0.1815$ | 0.9917 |
|  | ERG/GEF-LIP (pH 6.4) | $Y=0.4977x-0.1817$ | 0.9848 |

Fig. 12

| PC-9/GR resistance index | | |
|---|---|---|
| Cell type | IC50 (μM) | RI |
| PC-9 | 19.37 | 13.90 |
| PC-9/GR | 269.32 | |

Fig. 13

| Effect of different liposome groups on cell uptake rate ($\bar{x}\pm s$) | | | |
|---|---|---|---|
| Group | Uptake rate (%) | Average uptake rate (%) | Significance |
| control | 0.00 | 0.00±0.0 | |
| | 12.09 | | |
| LIP | 15.64 | 13.81±1.78 | ** |
| | 13.71 | | |
| | 74.11 | | |
| ERG-LIP | 73.40 | 73.25±0.95 | ** |
| | 72.23 | | |
| | 97.92 | | |
| ERG/GEF-LIP | 97.39 | 97.14±0.93 | ** |
| | 96.12 | | |

Fig. 14

Effect of protective agent addition on liposome freeze-drying

| Protective agent addition method | Appearance | Particle size (nm) | PDI |
|---|---|---|---|
| Internal addition method | Obviously collapse, shrink | 240.2±34.0 | 0.526±0.024 |
| External addition method | No collapse, slightly shrink | 163.4±1.3 | 0.297±0.016 |

Fig. 15

Effect of prefreezing rate on liposome freeze-drying

| Prefreezing rate | Appearance | Particle size (nm) | PDI |
|---|---|---|---|
| Quick-freezing method | Intact and loose, no collapse | 157.0±1.9 | 0.251±0.022 |
| Slow-freezing method | Slightly shrink | 178.7±2.4 | 0.261±0.044 |

Fig. 16

Effect of prefreezing time on liposome freeze-drying

| Prefreezing time (h) | Appearance | Particle size (nm) | PDI | ERG entrapment efficiency (%) | GEF entrapment efficiency (%) |
|---|---|---|---|---|---|
| Before freeze-drying | --- | 121.6±3.7 | 0.250±0.005 | 95.64 | 88.46 |
| 1 | shrink | 111.7±2.1 | 0.240±0.028 | 84.55 | 75.92 |
| 2 | shrink | 111.8±1.5 | 0.250±0.009 | 86.25 | 77.35 |
| 3 | shrink | 110.2±1.2 | 0.255±0.022 | 89.73 | 70.96 |
| 4 | Intact and loose, uniform and full | 119.5±2.5 | 0.243±0.004 | 90.60 | 83.44 |
| 6 | Intact and loose, uniform and full | 111.7±1.9 | 0.292±0.024 | 78.77 | 81.69 |
| 8 | shrink | 109.6±1.2 | 0.349±0.011 | 92.13 | 74.41 |

Fig. 17

Water content of freeze-dried powder at different freeze-drying time

| Freeze-drying time (h) | First stage (-20~-10°C) | Second stage (-10~0°C) | Third stage (0~10°C) | Fourth stage (10~20°C) | Fifth stage (20~30°C) | Water content (%) |
|---|---|---|---|---|---|---|
| 20 | 4 | 4 | 4 | 4 | 4 | 8.75 |
| 25 | 5 | 5 | 5 | 5 | 5 | 4.55 |
| 30 | 6 | 6 | 6 | 6 | 6 | 4.41 |
| 35 | 10 | 6 | 6 | 6 | 7 | 3.95 |
| 48 | 10 | 10 | 10 | 10 | 8 | 3.74 |
| 72 | 15 | 15 | 15 | 15 | 12 | 3.85 |

Fig. 18

Effects of different freeze-drying protective agents on liposome freeze-drying

| Protective agent | Appearance | Particle size (nm) | PDI | ERG entrapment efficiency (%) | GEF entrapment efficiency (%) |
|---|---|---|---|---|---|
| Before freeze-drying | — | 151.9±0.5 | 0.152±0.014 | 97.49 | 91.37 |
| glucose | More holes, shrink | 173.5±4.7 | 0.370±0.040 | 95.61 | 59.56 |
| Sucrose | Shrink | 128.9±1.7 | 0.164±0.030 | 95.99 | 69.55 |
| Lactose | Intact and loose, uniform and full | 167.3±0.9 | 0.241±0.015 | 76.68 | 42.33 |
| Mannitol | Intact and loose, uniform and full | 407.0±17.8 | 0.484±0.016 | 49.91 | 40.34 |
| Sorbitol | Shapeless | 241.9±4.9 | 0.527±0.028 | 85.90 | 40.31 |
| Xylitol | Shapeless | 339.0±38.5 | 0.620±0.099 | 90.03 | 45.63 |

Fig. 19

Addition and proportion of different freeze-drying protective agents

| Group | Ratio of carbohydrate to lipid | Sucrose : mannitol |
|---|---|---|
| 1 | 10:1 | 1:2 |
| 2 | 10:1 | 1:1 |
| 3 | 10:1 | 2:1 |
| 4 | 6:1 | 1:2 |
| 5 | 6:1 | 1:1 |
| 6 | 6:1 | 2:1 |
| 7 | 3:1 | 1:2 |
| 8 | 3:1 | 1:1 |
| 9 | 3:1 | 2:1 |

Fig. 20

Effects of combination of freeze-drying protective agents on liposome freeze-drying

| Group | Appearance | Rehydration time | Particle size (nm) | PDI | ERG entrapment efficiency (%) | GEF entrapment efficiency (%) |
|---|---|---|---|---|---|---|
| Before freeze-drying | — | — | 141.5±0.5 | 0.204±0.008 | 99.86 | 92.40 |
| 1 | Intact and loose, uniform and full | <5 min | 134.3±0.9 | 0.190±0.026 | 97.22 | 65.69 |
| 2 | Intact and loose, uniform and full | <15 s | 134.9±2.0 | 0.192±0.007 | 92.41 | 83.34 |
| 3 | Slightly shrink | <30 s | 127.1±3.1 | 0.192±0.019 | 95.63 | 69.02 |
| 4 | Intact and loose, uniform and full | <3 min | 133.0±2.8 | 0.189±0.008 | 86.80 | 69.63 |
| 5 | More holes, shrink | <40 s | 131.2±2.5 | 0.201±0.023 | 86.97 | 72.51 |
| 6 | Shrink | <4 min | 126.5±2.1 | 0.192±0.012 | 82.56 | 69.37 |
| 7 | Intact and loose, uniform and full | <1 min | 134.4±2.4 | 0.208±0.011 | 94.63 | 72.71 |
| 8 | Shrink | <15 s | 145.8±1.5 | 0.249±0.018 | 72.24 | 67.98 |
| 9 | Unformed, and quickly absorb moisture | <1 min | 130.5±1.2 | 0.204±0.013 | 70.94 | 73.21 |

Fig. 21

Prescription optimization verification test

| Group | Appearance | Rehydration time | Particle size (nm) | PDI | ERG entrapment efficiency (%) | GEF entrapment efficiency (%) |
|---|---|---|---|---|---|---|
| Before freeze-drying | — | — | 153.8±0.6 | 0.243±0.013 | 101.08 | 90.88 |
| 2 |  |  | 138.0±0.3 | 0.213±0.007 | 94.76 | 80.72 |
| 2 |  | <15 s | 137.5±1.4 | 0.207±0.012 | 95.02 | 81.35 |
| 2 |  |  | 135.6±1.6 | 0.212±0.012 | 93.09 | 79.44 |
| 4 |  |  | 145.9±2.0 | 0.206±0.018 | 84.62 | 74.79 |
| 4 | Intact and loose, uniform and full | <1 min | 145.3±1.5 | 0.220±0.019 | 97.51 | 76.03 |
| 4 |  |  | 148.3±1.9 | 0.217±0.024 | 86.92 | 74.40 |
| 7 |  |  | 159.2±2.8 | 0.259±0.011 | 68.80 | 74.19 |
| 7 |  | <30 s | 157.1±1.9 | 0.279±0.018 | 69.99 | 73.95 |
| 7 |  |  | 158.4±2.5 | 0.252±0.014 | 79.15 | 75.94 |

Fig. 22

Changes in particle size and zeta potential of RGD/R8-ERG/GEF-LIP and its freeze-dried powder in serum

| Time (h) | RGD/R8-ERG/GEF-LIP | | | RGD/R8-ERG/GEF-LIP freeze-dried powder | | |
|---|---|---|---|---|---|---|
| | Particle size (nm) | PDI | Potential (mV) | Particle size (nm) | PDI | Potential (mV) |
| 0 | 161.8±2.3 | 0.236±0.008 | -13.6±0.6 | 144.7±1.1 | 0.224±0.003 | -13.4±0.4 |
| 0.5 | 160.7±1.5 | 0.236±0.004 | -12.2±0.9 | 146.0±0.7 | 0.216±0.012 | -12.9±0.5 |
| 1 | 158.9±2.7 | 0.240±0.014 | -13.2±0.2 | 145.9±0.9 | 0.216±0.005 | -12.6±1.0 |
| 2 | 162.9±1.1 | 0.249±0.008 | -13.5±0.6 | 144.2±0.8 | 0.204±0.012 | -14.1±1.7 |
| 4 | 160.4±2.1 | 0.267±0.024 | -13.7±0.8 | 144.5±0.8 | 0.241±0.020 | -12.7±0.6 |
| 8 | 147.5±1.9 | 0.260±0.008 | -14.1±0.6 | 143.6±2.3 | 0.245±0.025 | -12.8±1.1 |
| 24 | 143.1±2.6 | 0.268±0.020 | -18.2±0.9 | 143.3±2.8 | 0.270±0.021 | -15.9±0.6 |

Fig. 23

Model formula

| Model | Model equation |
|---|---|
| Zero-order model | $Y=kt+k_1$ |
| First-order model | $\ln(1-Y)=-kt+k_1$ |
| Higuchi model | $Y=kt^{1/2}+k_1$ |

Fig. 24

Fitting results and correlation coefficients of cumulative drug release rate

| Model | Drugs | Fitting equation | $R^2$ |
|---|---|---|---|
| Zero-order model | GEF drug substance (pH 7.4) | Y=0.1131t+0.3394 | 0.9065 |
| | GEF drug substance (pH 6.4) | Y=0.0989t+0.5139 | 0.8897 |
| | Freeze-dried powder (pH 7.4) | Y=0.1136t+0.1652 | 0.9241 |
| | Freeze-dried powder (pH 6.4) | Y=0.1426t+0.2247 | 0.9248 |
| First-order model | GEF drug substance (pH 7.4) | Y=-0.2708t-0.3649 | 0.9680 |
| | GEF drug substance (pH 6.4) | Y=-0.3713t-0.6344 | 0.9807 |
| | Freeze-dried powder (pH 7.4) | Y=-0.1899t-0.1543 | 0.9633 |
| | Freeze-dried powder (pH 6.4) | Y=-0.3094t-0.1879 | 0.9856 |
| Higuchi model | GEF drug substance (pH 7.4) | Y=0.3007t+0.1745 | 0.9684 |
| | GEF drug substance (pH 6.4) | Y=0.2654t+0.3670 | 0.9681 |
| | Freeze-dried powder (pH 7.4) | Y=0.3016t+0.00006 | 0.9843 |
| | Freeze-dried powder (pH 6.4) | Y=0.3786t+0.0173 | 0.9853 |

Fig. 25

Apoptosis rate of PC-9/GR cells

| Group | Drug concentration (µg · mL-1) | | Apoptotic rate (%) |
|---|---|---|---|
| | ERG | GEF | |
| Control | — | — | 1.71±0.47 |
| ERG/GEF-LIP | 16 | 20 | 22.41±0.32** |
| RGD-ERG/GEF-LIP | 16 | 20 | 29.63±0.77** |
| R8-ERG/GEF-LIP | 16 | 20 | 32.27±0.60** |
| RGD/R8-ERG/GEF-LIP | 16 | 20 | 37.40±0.89**△△** |
| RGD/R8-ERG/GEF-LIP freeze-dried powder | 16 | 20 | 37.88±1.79**△△** |

Fig. 26

The change of body mass in nude mice ($\bar{x}\pm s$)

| Group | Body weight (g) | | | | | | |
|---|---|---|---|---|---|---|---|
| | Day 1 | Day 3 | Day 5 | Day 9 | Day 11 | Day 13 | Day 15 |
| Normal control group | 26.07±1.48 | 26.23±1.62 | 26.47±1.46 | 26.83±1.19 | 27.10±1.66 | 27.10±1.94 | 27.37±1.96* |
| Model control group | 25.00±0.94 | 25.46±1.08 | 26.10±1.05 | 26.50±1.01 | 26.82±0.92 | 26.72±1.21 | 26.28±1.12* |
| Positive drug group | 24.94±2.55 | 26.19±3.14 | 27.13±2.11 | 27.13±2.00 | 27.80±1.98 | 27.98±1.71 | 28.60±1.78** |
| ERG/GEF-LIP | 24.60±1.17 | 25.18±1.06 | 25.38±1.09 | 25.86±2.13 | 26.04±1.68 | 26.32±1.75 | 26.48±1.60** |
| RGD/R8-ERG/GEF-LIP | 24.20±0.28 | 24.88±0.22 | 25.36±0.52 | 25.84±0.78 | 26.32±0.90 | 26.86±1.08 | 27.14±1.44** |
| RGD/R8-ERG/GEF-LIP freeze-dried powder | 24.96±1.23 | 25.44±1.80 | 26.22±1.11 | 26.24±0.98 | 26.76±0.99 | 26.83±1.17 | 27.82±1.38** |

Fig. 27

The change of tumor volume in nude mice of each group ($\bar{x}\pm s$)

| Group | Tumor volume (mm³) | | | | | | |
|---|---|---|---|---|---|---|---|
| | Day 1 | Day 3 | Day 5 | Day 9 | Day 11 | Day 13 | Day 15 |
| Model control group | 530.60±23.51 | 651.70±91.85 | 785.33±126.33 | 863.01±134.86 | 859.98±138.67 | 1006.04±127.31 | 1235.40±74.01 |
| Positive drug group | 530.09±23.93 | 629.18±20.33 | 673.82±66.30 | 713.25±128.48 | 719.04±129.19 | 873.52±107.26 | 990.56±119.91 |
| ERG/GEF-LIP | 509.49±75.50 | 642.95±93.98 | 619.67±64.89 | 693.84±29.51 | 783.79±46.52 | 913.45±16.26 | 917.97±62.62* |
| RGD/R8-ERG/GEF-LIP | 503.44±55.78 | 581.80±64.12 | 631.68±63.85 | 685.36±31.85 | 730.60±59.32 | 852.34±38.54 | 865.73±56.00** |
| RGD/R8-ERG/GEF-LIP freeze-dried powder | 506.42±43.65 | 535.56±29.17 | 579.42±65.11 | 749.48±47.12 | 750.30±38.38 | 797.28±56.04 | 821.72±78.59** |

Fig. 28

The average tumor weight and the inhibitory rate in nude mice of each group ($\bar{x}\pm s$)

| Group | Average tumor weight (mg) | Tumor inhibitory rate (%) |
|---|---|---|
| Model control group | 797.30±130.84 | — |
| Positive drug group | 622.60±50.47** | 21.91 |
| ERG/GEF-LIP | 586.72±31.23** | 26.41 |
| RGD/R8-ERG/GEF-LIP | 517.54±94.14** | 35.09 |
| RGD/R8-ERG/GEF-LIP freeze-dried powder | 529.54±55.51** | 33.58 |

Fig. 29

The spleen index in nude mice of each group ($\bar{x}\pm s$)

| Group | Spleen index (mg·g$^{-1}$*10) |
|---|---|
| Blank control group | 38.97±9.92 |
| Model control group | 36.81±1.88 |
| Positive drug group | 27.11±2.06^△ |
| ERG/GEF-LIP | 63.05±5.92**^△△** |
| RGD/R8-ERG/GEF-LIP | 42.31±7.21** |
| RGD/R8-ERG/GEF-LIP freeze-dried powder | 38.57±5.17* |

Fig. 30

The content of IL-2, TGF-β1, TIMPs, TNF-α in serum alpha in nude mice of each group ($\bar{x} \pm s$)

| Group | IL-2 content (ng·L⁻¹) | TGF-β1 content (pg·mL⁻¹) | TIMPs content (ng·mL⁻¹) | TNF-α content (ng·L⁻¹) |
|---|---|---|---|---|
| Blank control group | 82.63±13.54 | 100.92±10.38 | 31.85±4.75 | 721.62±84.90 |
| Model control group | 147.69±34.16** | 171.29±25.55** | 54.43±12.24** | 881.46±43.26** |
| Positive drug group | 107.54±7.81△△ | 133.80±7.47△△ | 43.39±3.99△△ | 824.71±36.22 |
| ERG/GEF-LIP | 101.44±9.74△△ | 122.72±12.39△△ | 39.55±4.93△△ | 827.19±112.34 |
| RGD/R8-ERG/GEF-LIP | 94.44±8.01△△ | 105.13±15.57△△** | 36.06±4.64△△* | 763.49±66.00△ |
| RGD/R8-ERG/GEF-LIP freeze-dried powder | 96.65±12.39△△ | 109.26±10.38△△** | 36.02±5.89△△ | 762.32±77.27△△ |

Fig. 31

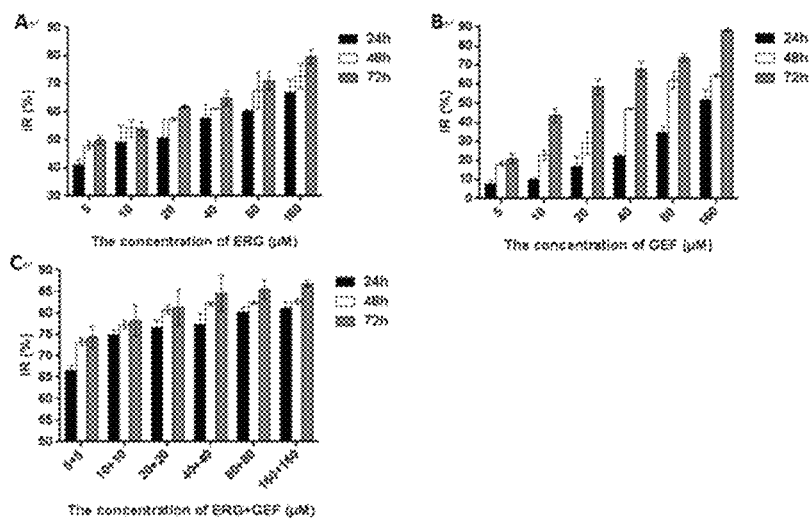

A: Inhibitory rate results of ERG group; B: Inhibitory rate results of GEF group; C: Inhibitory rate results of ERG+GEF group Inhibitory rate on A549 lung cancer cells treated with different drugs at different time points

Fig. 32

A: Inhibitory rate results of ERG group; B: Inhibitory rate results of GEF group;
C: Inhibitory rate results of GEF+ERG group Inhibitory rate on PC-9 lung cancer cells treated with different drugs at different time points A: Normal control group B: ERG (20 μM); C: GEF (20 μM); D: ERG+GEF (20+20 μM)

Nuclei of A549 cells stained with ERG and GEF

A: Normal control group B: ERG (40 μM); C: GEF (5 μM); D: ERG combined with GEF (40+5μM)

Nuclei of PC-9 cells stained with ERG and GEF

A: Expression of p-AKT/AKT protein on A549 cells; B: Expression of p-EGFR/EGFR protein on A549 cells C: Expression of p-AKT/AKT protein on PC-9 cells; D: Expression of p-EGFR/EGFR protein on PC-9 cells Expression of ERG and GEF on A549 and PC-9 cells (a) and quantitative analysis (b)

1: LIP; 2: ERG-LIP; 3: ERG/GEF-LIP

Appearance of liposomes

LIP　　　　　　ERG-LIP　　　　　　ERG/GEF-LIP

The transmission electron microscopy picture of the liposomes

A: LIP; B: ERG-LIP; C: ERG/GEF-LIP

The Zeta potential of liposomes

Accumulative release of GEF and ERG/GEF-LIP in different pH release media.

Inhibitory effect of GEF on proliferation of sensitive and drug-resistant cells.

The cooling-rate curve of sample and cold trap

1: RGD-ERG/GEF-LIP; 2: R8-ERG/GEF-LIP; 3: RGD/R8-ERG/GEF-LIP;

4: Redissolved RGD/R8-ERG/GEF-LIP freeze-dried powder; 5: RGD/R8-ERG/GEF-LIP freeze-dried Appearance of liposomes The transmission electron microscopy picture of the liposomes Investigation of serum stability of RGD/R8-ERG/GEF-LIP and its lyophilized powder Accumulative release of GEF and ERG/GEF-LIP freeze-dried powders in different pH release media 24 h MTT test results of raw medicine and liposomes Fluorescence uptake intensity of fluorescent drug-loaded liposomes A: Control; B: ERG/GEF-LIP; C: RGD-ERG/GEF-LIP; D: R8-ERG/GEF-LIP; E: RGD/R8-ERG/GEF-LIP;

F: RGD/R8-ERG/GEF-LIP freeze-dried powder

Apoptosis flow pattern of PC-9/GR cells

The change of body mass in nude mice ($\bar{x}\pm s$)

USES OF ERGOSTEROL COMBINED WITH GEFITINIB, PREPARATION METHODS OF LIPOSOME AND FREEZE-DRIED POWDER THEREOF

TECHNICAL FIELD

The present disclosure relates to a drug combination for treating non-small cell lung cancer, in particular to uses of ergosterol combined with gefitinib, and belongs to the technical field of biomedicine.

BACKGROUND ART

Due to the continuous increase in cancer incidence and mortality, it is still one of the most concerned problems in the world. According to statistics, about 4.3 million new cancer cases were diagnosed, and about 2.81 million cancer patients died in China in 2015, of which lung cancer ranked first. *The Global Cancer Statistics* 2018: *GLOBOCAN Estimates of Incidence and Mortality Worldwide*, compiled by the International Agency for Research on Cancer, provided a status report on the global burden of cancer that is expected to have 18.1 million new cancer cases and 9.6 million cancer death cases in 2018. Among them, lung cancer is the most common cancer (11.6% of the total cases) and the leading cause of cancer death (18.4% of total cancer deaths). It has been found clinically that lung adenocarcinoma has gradually replaced squamous cell lung carcinoma as the pathological type with the highest incidence of lung cancer, accounting for about half of NSCLC, while NSCLC accounts for about 85% of all lung cancers.

At present, clinical first-line chemotherapy drugs (platinum, adriamycin, paclitaxel, etc.) will have multi-drug resistance during chemotherapy, which will eventually lead to further disease progression. GEF is the first molecular targeted drug for treating NSCLC, and is commonly used as a second-line therapeutic drug in the clinical application at present. GEF is an epidermal growth factor receptor (EGFR) tyrosine kinase inhibitor, and has better clinical therapeutic effects on EGFR targeted NSCLC. The mechanism of action of GEF is mainly that through competition with adenosine triphosphate (ATP) and binding to EGFR, an EGFR signal transduction pathway is blocked through AKT and other pathways, the autophosphorylation and activation are inhibited, the growth of tumor cells expressing EGFR is blocked, a downstream signal pathway such as PI3K-AKT is blocked, and the apoptosis of tumor cells is induced to play an anti-tumor effect. For patients with EGFR mutations, the occurrence degree of GEF side effects is significantly reduced compared with chemotherapy. At the same time, studies have shown that mutations in an EGFR gene are more observed in female patients, Asian patients, and non-smokers. Reports show that lung cancer patients in Eastern countries tend to have better GEF clinical therapeutic effects than Western countries. It can be seen that the in-depth study of GEF is of great significance to Asian NSCLC patients.

For lung cancer, it is of great value to find a drug that can generate synergy with GEF, expand the application range of GEF, and improve the clinical application of targeted drugs in the treatment of lung cancer.

SUMMARY OF THE DISCLOSURE

In order to solve the above problems, in the present disclosure, the mechanism of action that ergosterol (ERG) combined with gefitinib (GEF) induces apoptosis of non-small cell lung cancer (NSCLC) cells is firstly studied; then an RGG cyclic peptide/R8 peptide modified ERG combined with GEF active drug-loaded targeted liposome delivery system (RGD/R8-ERG/GEF-LIP) is constructed; and RGD/R8-ERG/GEF-LIP is prepared into freeze-dried powder to improve stability, quality evaluation and preliminary evaluation of in vitro anti-lung cancer effects are conducted, and a nude mouse lung cancer xenograft model is established for conducting preliminary pharmacodynamic research and in vivo targeting research.

The technical scheme of the present disclosure to solve the above problems is as follows:

Uses of ergosterol combined with gefitinib in the preparation of a drug for treating non-small cell lung cancer are provided.

Preferably, the therapeutic mechanism is based on the synergistic inhibitory effect of ergosterol combined with gefitinib on PC-9 cells and/or A549 cells.

Preferably, the therapeutic mechanism is based on the synergistic apoptosis-inducing effect of ergosterol combined with gefitinib on PC-9 cells and/or A549 cells.

Preferably, the synergistic inhibitory effect is based on the combination of ergosterol and gefitinib to increase G0/G1 phase arrest and reduce the S phase fraction of cell cycle on A549 cells and/or PC-9 cells.

Preferably, the synergistic apoptosis-inducing effect is based on the combination of ergosterol and gefitinib to inhibit expression of an EGFR signal pathway on A549 cells and/or PC-9 cells.

Preferably, the EGFR signal pathway is a P13K/AKT/mTOR signal pathway.

Preferably, the ergosterol has a drug concentration of 5 to 320 μM, and the gefitinib has a drug concentration of 0.625 to 40 μM.

Preferably, the ergosterol has a drug concentration of 20 to 40 μM, and the gefitinib has a drug concentration of 2.5 to 5 μM.

Preferably, the ergosterol has a drug concentration of 20 to 80 μM, and the gefitinib has a drug concentration of 5 to 40 μM.

Another objective of the present disclosure is to provide a preparation method of an ergosterol-gefitinib combined liposome. The ERG-GEF combined compound liposome is prepared by entrapping GEF by an ammonium sulfate gradient method. The specific preparation process includes the following steps: fully dissolving SPC and Chole at a molar ratio of (3 to 7):1, and ERG with a drug loading capacity of 5 to 15 wt % in chloroform, placing on a rotary evaporator in a 30 to 50° C. water bath to spin-dry, drying in vacuum to be odorless; adding pure water and placing on a horizontal shaker to be hydrated for 20 to 50 min at a rotational speed of 100 to 200 rpm/mL to obtain an intermediate product; placing the intermediate product under an ice bath, ultrasonically treating with a probe for 10 to 30 min, ultrasonically treating for 1 to 5 s, and stopping for 0.5 to 2 s; sequentially filtering by using multistage microfiltration membranes and finally extruding under high pressure with a 0.1 μm polycarbonate membrane to obtain the ERG-GEF combined liposome.

Preferably, the molar ratio of SPC to Chole is 5:1.
Preferably, the drug loading capacity of ERG is 10 wt %.
Preferably, the rotational speed is 130 to 160 rpm/mL.
Preferably, the multistage microfiltration membranes are 0.8 μm, 0.45 μm, and 0.22 μm, respectively.
Preferably, the concentration of ammonium sulfate is 150 to 250 mM.
Preferably, the incubation temperature is 30 to 50° C.

Preferably, the concentration ratio of ERG to GEF is (1.5 to 6):1.

Another objective of the present disclosure is to provide an ergosterol-gefitinib combined liposome prepared by the above method.

Preferably, the average particle size of the liposome is 145.2±1.0 nm; the polydispersity index PDI is 0.199±0.036; the Zeta potential of the liposome is −19.0±3.1 mV; pH is 5.05±0.12; the average hydrogen peroxide value is 0.0237±0.0018; the entrapment efficiency is 95.33±0.21%, and the drug loading capacity is 3.94±0.10%.

A further objective of the present disclosure is to provide a preparation method of freeze-dried powder of the ergosterol-gefitinib combined compound liposome, including: adding a freeze-drying protective agent to a pre-prepared RGD/R8-ERG/GEF-LIP liposome suspension by an external addition method; and then preparing the freeze-dried powder of the compound liposome by a freeze-drying method; the RGD/R8-ERG/GEF-LIP liposome suspension is prepared by the following method, including: firstly preparing ERG/GEF-LIP, and preparing the RGD/R8-ERG/GEF-LIP liposome suspension by a post-insertion method.

Preferably, the freeze-drying method is specifically a quick-freezing method, specifically including: pre-lowering the temperature of a cold trap portion in equipment to a minimum temperature, and then placing a sample in the cold trap.

Preferably, the prefreezing time of the freeze-drying method is 4 h.

Preferably, the freeze-drying time of the freeze-drying method is 48 h.

Preferably, the freeze-drying protective agent is a combination of sucrose and mannitol, and the ratio of carbohydrate to lipid is 10:1, and the mass ratio of sucrose to mannitol is 1:1.

Preferably, the preparation method of the RGD/R8-ERG/GEF-LIP liposome suspension specifically includes: weighing SPC, Chole and RGD peptide according to a molar ratio of 5:1:0.07 to prepare R8-ERG/GEF-LIP; weighing SPC, Chole, RGD peptide and RGD peptide according to a molar ratio of 5:1:0.07:0.07 to prepare the RGD/R8-ERG/GEF-LIP liposome suspension.

Preferably, the quick-freezing method is used, including: placing the sample at the cold trap in the equipment for 4 h, transferring to the upper layer for freeze-drying, and the freeze-drying procedure is as follows: −20 to −10° C., 15 h; −10 to 0° C., 15 h; 0 to 10° C., 15 h; 10 to 20° C., 15 h; and 20 to 30° C., 12 h.

Another objective of the present disclosure is to provide liposome freeze-dried powder prepared by the above method.

A still another objective of the present disclosure is to provide application of the liposome freeze-dried powder in the preparation of a targeted drug for inhibiting tumor cell growth and/or inducing tumor cell apoptosis.

The present disclosure has the following beneficial effects that:

1. Inhibitory effects of a drug on tumor are studied by in vitro culture of lung cancer A549 cells and PC-9 cells in the present disclosure. Two cell lines (GEF-sensitive PC-9 cells and drug-resistant A549 cells, respectively) are used for an MTT test; Hochest33258 cell apoptosis test is conducted; the cell apoptosis and the cell cycle are detected by flow cytometry; and the effects of cellular EGFR signal pathway are investigated by a Western-blots test. It is concluded that the combination of ERG and GEF has a synergistic anti-lung cancer effect, which proves to a certain extent that it has synergistic and sensitizing effects on GEF-sensitive PC-9 cells, and can increase certain sensitivity on GEF-resistant A549 cells.

2. GEF is entrapped by the ammonium sulfate gradient method to prepare the ERG-GEF combined compound liposome (ERG/GEF-LIP) in the present disclosure. The preparation process of ERG/GEF-LIP is optimized by a single factor and response surface design using GEF entrapment efficiency as an index, the morphology, particle size distribution, Zeta potential, in vitro cumulative release rate, and peroxide value thereof are preliminarily investigated, and the preliminary in vitro anti-lung cancer research on drug-resistant cells PC-9/GR is conducted.

3. The RGD/R8-ERG/GEF-LIP active drug-loaded liposome delivery system is successfully constructed in the present disclosure; the freeze-drying process and prescription are investigated by the ERG/GEF-LIP, and the best prescription and process are screened out and applied to RGD/R8-ERG/GEF-LIP for verification. The in vitro test results of RGD/R8-ERG/GEF-LIP freeze-dried powder confirm that it has stronger tumor cell proliferation inhibitory effects, fluorescence uptake intensity and good apoptotic rate.

4. Related in vivo research is conducted in the present disclosure wherein the preliminary pharmacodynamic test indicates that the RGD/R8-ERG/GEF-LIP freeze-dried powder has no significant toxic and side effects on nude mice and does not cause adverse effects such as mental disorders and weight loss of nude mice during administration, and the in vivo tumor inhibitory effects of RGD/R8-ERG/GEF-LIP freeze-dried powder and RGD/R8-ERG/GEF-LIP have little difference. It indicates that when RGD/R8-ERG/GEF-LIP is prepared into a freeze-dried powder form, the inhibitory effect of the liposome on PC-9/GR lung cancer xenografts in nude mice cannot be affected. The targeting test also confirms that the prepared drug-loaded liposome has certain targeting ability.

5. In the present disclosure, based on the mechanism of action that the GEF combined with ERG induces the apoptosis of non-small cell lung cancer cells in vitro, the RGD/R8-ERG/GEF-LIP active drug-loaded targeted liposome delivery system is constructed, and is prepared into the freeze-dried powder form, preliminary evaluation of in vitro and in vivo anti-lung cancer effects is carried out, and a nude mouse lung cancer xenograft model is established for preliminary pharmacodynamic research and in vivo targeting research. The optimal preparation process and quality evaluation of ERG/GEF-LIP show that GEF is loaded on ERG/GEF-LIP by the ammonium sulfate gradient method. The liposome is round in morphology and has a two-layer structure, and the particle size is uniformly distributed. In a pH 6.4 release medium, the cumulative release rate within 24 h of ERG/GEF-LIP exceeds 80%. The average entrapment efficiency of GEF is 96.49±1.00%, and the drug loading capacity is 5.73±0.62%. The average entrapment efficiency of ERG is 95.33±0.21%, and the drug loading capacity is 3.94±0.10%. The in vitro experiment shows that the resistance index of PC-9/GR cells is 13.90, and the cells are highly resistant to drugs. Proliferation inhibitory effects on PC-9/GR cells and fluorescence uptake intensity of ERG/GEF-LIP are the strongest. The preparation and quality evaluation of the RGD/R8-ERG/GEF-LIP freeze-dried powder show that RGD/R8-ERG/GEF-LIP is prepared by the post-insertion method, the RGD/R8-ERG/GEF-LIP freeze-dried powder is prepared by prefreezing for 4 h, and freeze-drying for 48 h by using the quick-freezing method, and each liposome freeze-dried powder (5 mL) contains 245 mg of sucrose and 245 mg of mannitol (the ratio of carbohydrate to lipid is 10:1, and the mass ratio of sucrose to mannitol is 1:1). The liposome is round in morphology and has a two-layer structure, and the particle size is uniformly distributed. In the pH 6.4 release medium, the cumulative release rate within 24 h of the RGD/R8-ERG/GEF-LIP freeze-dried powder exceeds 80%, and it has good serum stability. The average entrapment efficiency of GEF is 80.50±0.98%, and the drug loading capacity is 4.67±0.17%. The average entrapment efficiency of ERG is 94.29±1.04%, and the drug loading capacity is 3.59±0.41%. The in vitro experiment shows that the proliferation inhibitory effects on the PC-9/GR cells, fluorescence uptake intensity and cell apoptotic rate of the RGD/R8-ERG/GEF-LIP freeze-dried powder are all higher, and nearly have no difference before freeze-drying. The tumor inhibitory effect in nude mice and in vivo targeting research of the RGD/R8-ERG/GEF-LIP freeze-dried powder show that in the preliminary pharmacodynamic test of the RGD/R8-ERG/GEF-LIP freeze-dried powder in PC-9/GR tumor-bearing nude mice, there is no significant change in body mass of nude mice in each administration group, and both the RGD/R8-ERG/GEF-LIP group and the RGD/R8-ERG/GEF-LIP freeze-dried powder group have obvious tumor inhibitory effects. The spleen index of each liposome administration group is significantly higher than that of a positive drug group. The levels of IL-2, TGF-β1, TIMPs and TNF-α in serum in a model group are all higher than those in a blank control group. After administration, the indexes of each component are decreased to different extents, suggesting that the drug has certain anti-lung cancer effects. The results of pathological section show that the necrotic area of the tumor tissue in each administration group is increased, and the spleen and lung tissues have normal morphological characteristics. In vivo targeting research results have shown that fluorescence is accumulated in the tumor site, and the prepared drug-loaded liposome has certain targeting ability.

BRIEF DESCRIPTION OF THE DRAWINGS

FIG. 1 shows 549 cell inhibitory rates of two single drug groups and a combination group at different time points of action;
FIG. 2 shows the $IC_{50}$ values of two single drug groups at different time points of action;
FIG. 3 shows q values of synergistic inhibitory effect of ERG combined with GEF on A549 cells;
FIG. 4 shows PC-9 cell inhibitory rates of two single drug groups and a combination group at different time points of action;
FIG. 5 shows $IC_{50}$ values of two single drug groups at different time points of action;
FIG. 6 shows q values of synergistic inhibitory effects of ERG combined with GEF on A549 cells;
FIG. 7 shows apoptotic rates of A549 cells acted by ERG and GEF;
FIG. 8 shows apoptotic rates of PC-9 cells acted by ERG and GEF;
FIG. 9 shows the cycle distribution of A549 cells acted by ERG and GEF;
FIG. 10 shows the cycle distribution of PC-9 cells acted by ERG and GEF;
FIG. 11 shows a model formula;
FIG. 12 shows the fitting results and correlation coefficients of cumulative release rates of drugs;
FIG. 13 shows PC-9/GR resistance indexes;
FIG. 14 shows effects of different liposome administration groups on cell uptake rates;
FIG. 15 shows the effects of the addition method of a protective agent on the freeze-drying effect of a liposome;
FIG. 16 shows the effects of prefreezing rate on the freeze-drying effect of a liposome;
FIG. 17 shows the effects of prefreezing time on the freeze-drying effect of a liposome;
FIG. 18 shows the water contents of the freeze-dried powder with different freeze-drying times;
FIG. 19 shows effects of different freeze-drying protective agents on the freeze-drying effect of a liposome;
FIG. 20 shows the addition amount and proportion of different freeze-drying protective agents;
FIG. 21 shows the effects of a combination of freeze-drying protective agents on the freeze-drying effect of a liposome;
FIG. 22 shows a prescription optimization verification test;
FIG. 23 shows the changes in particle size and potential of RGD/R8-ERG/GEF-LIP and freeze-dried powder thereof in serum;
FIG. 24 shows a model formula;
FIG. 25 shows fitting results and correlation coefficients of cumulative release rates of drugs;
FIG. 26 shows apoptotic rates of PC-9/GR cells;
FIG. 27 shows changes in body mass of nude mice in each group;
FIG. 28 shows a tumor growth curve of nude mice in each group;
FIG. 29 shows the average tumor weight and tumor inhibitory rate of nude mice in each group;
FIG. 30 shows the spleen index of nude mice in each group;
FIG. 31 shows the contents of IL-2, TGF-β1, TIMPs and TNF-α in serum of nude mice in each group;
FIG. 32 shows inhibitory rates on A549 lung cancer cells at different drug action times.

DETAILED DESCRIPTION OF THE DISCLOSURE

Figure 33:
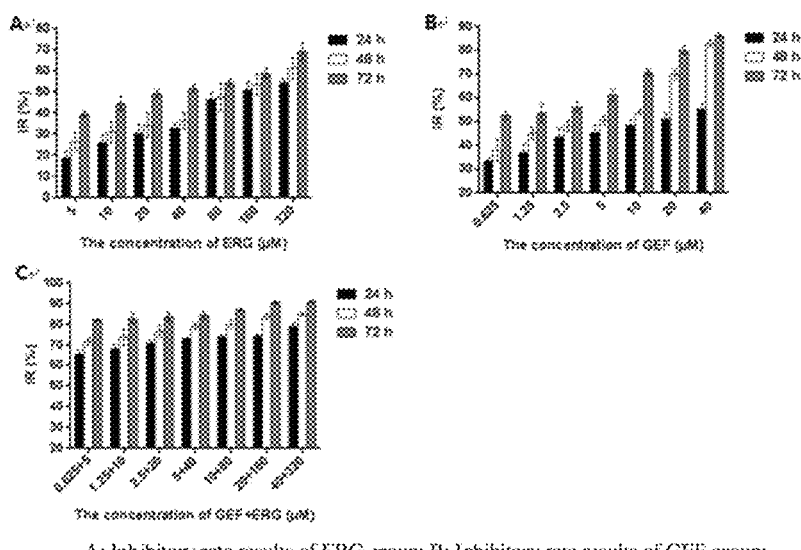
FIG. 33 shows inhibitory rates on PC-9 lung cancer cells at different drug action times.

The present disclosure is further explained below in conjunction with the drawings.

Research on Mechanism of Action of Ergosterol Combined with Gefitinib in Inducing Apoptosis of Non-small Cell Lung Cancer Cells in vitro (I) Cell Culture Cells were inoculated into a cell culture flask, added with a 5 to 6 ml complete medium containing 10% fetal bovine serum (FBS), and placed in a 37° C. 5% $CO_2$ incubator after blowing well, the cell growth state was observed every day, the medium was replaced once every 2 to 3 days, and cell passage or cryopreservation were performed when the cells were grown to about 80% of the bottom area of the culture flask.

(II) Cell Subculture

Cell subculture was performed when the cells were grown to 80% as follows: the medium was discarded, and the cells were washed 3 times with phosphate buffered saline (PBS), about 2 ml each time. After discarding the PBS, 1 ml of a 0.25% trypsin solution was added, and after cell digestion was completed, a culture solution was added to terminate the digestion. After centrifuging at 800 rpm·min$^{-1}$ for 5 min, a supernatant was discarded, a medium containing 10% FBS was added to blow well, and the cells were counted by a cell counting plate, and subcultured in separate bottles.

(III) Cell Cryopreservation

The cells were collected and counted, added with 1.0 ml of a cryopreservation solution (90% FBS+10% dimethyl sulfoxide) and transferred into a cryogenic tube, then programmed gradient freezing was performed by placing at a temperature of 4° C. for 0.5 h, placing at a temperature of −20° C. for 1-2 h, putting in a −80° C. ultra-low temperature freezer to be preserved overnight, and then transferring to a −196° C. liquid nitrogen tank to be preserved.

(IV) Research on Inhibitory Effects of ERG Combined with GEF on Proliferation of A549 and PC-9 Cells (MTT Test)

The concentration of an A549 cell suspension in logarithmic growth phase was adjusted to $5 \times 10^4 \cdot mL^{-1}$. After centrifuging at 800 rpm·min$^{-1}$ for 5 min, a single cell suspension was formed by blowing, beating and mixing well, 100 μL of the single cell suspension was added to each well in a 96-well culture plate, the cells were cultured in a 37° C. 5% $CO_2$ incubator until 80% of the cells were fused and then a drug was added for treatment. Among them, 100 μL of different concentrations of PBS-free drug solutions were added in each administration group, and 100 μL of an FBS-free medium was added to a normal control group. 5 replicate wells were respectively arranged for each concentration, and MTT assay was performed at 24, 48, and 72 h after administrating. 20 μL, of an MTT (5 mg·mL$^{-1}$) solution was added to each well, and after incubating at a temperature of 37° C. for 4 h, the absorbance OD value of each well was measured at 492 nm using Elisa and verified at 570 nm. The inhibitory rate (IR) value at each concentration and the 50% inhibition concentration $IC_{50}$ value of the drug in each group were calculated, and the properties of combination of ERG and GEF were judged by using the q value. This experiment was repeated 3 times.

$$\text{Inhibitory rate} IR\ (\%) = \frac{\text{Control group} OD - \text{Experimental group} OD}{\text{Control group} OD} \times 100\%$$

$$q = \frac{E_{AB}}{E_A + E_B - E_A \times E_B}$$

where $E_A$ and $E_B$ are the inhibitory rate of a single drug, and $E_{AB}$ is the inhibitory rate of combination of two drugs. q>1.15 means a synergistic effect, q=0.85 to 1.15 means an additive effect, and q<0.85 means an antagonistic effect.

The results for human lung cancer A549 cells were as follows. The cell inhibitory rates of ERG group, GEF group and ERG+GEF group at different time points were investigated. The inhibitory rate of combination of two drugs was higher than that of the single drug group, and showed certain concentration dependence. The results are shown in FIG. 32, FIG. 1 and FIG. 2. When the incubation time was 48 h, the q value of the ERG+GEF combination group (20+20 μM) was greater than 1.15 (FIG. 3), indicating that the two drugs in combination have a synergistic effect. The concentration was the maximum concentration at which the two drugs had the synergistic effect, and when the concentration was increased, the two drugs only had an additive effect. Therefore, the subsequent experiment was performed by using the concentration as an intermediate concentration.

The results for human lung cancer PC-9 cells were as follows. The inhibitory rate of the GEF group on PC-9 cells at the same concentration was significantly higher than that on A549 cells (P<0.01). After being combined with ERG, the inhibitory rate of the ERG+GEF group was improved to a certain extent compared with the same concentration of the single drug group. The results are shown in FIG. 33, FIG. 4 and FIG. 5. When the incubation time was 48 h, the q value of the GEF+ERG combination group (5+40 μM) was greater than 1.15 (FIG. 6), indicating that the two drugs in combination have a synergistic effect The concentration was the maximum concentration at which the two drugs had the synergistic effect, and when the concentration was increased, the two drugs only had an additive effect. Therefore, the subsequent experiment was performed by using the concentration as an intermediate concentration.

(V) Research on Hoechst 33258 Apoptotic Staining of A549 and PC-9 Cells by ERG Combined with GEF The experiment was divided into 4 groups: group A (normal control group), group B (ERG group 20 μM), group C (GEF group 20 μM), and group D (ERG+GEF group 20+20 μM). The concentration of the A549 cell suspension in logarithmic growth phase was adjusted to $2 \times 10^5 \cdot mL^{-1}$. After centrifuging at 800 rpm·min$^{-1}$ for 5 min, a single cell suspension was formed by blowing, beating and mixing well, 2 mL of a drug-containing medium was added to each well in a 6-well culture plate, and 3 replicate wells were arranged for each drug. The cells were cultured in a 37° C. 5% $CO_2$ incubator until 80% of the cells were fused and then a drug was added for treatment. After 48 h, the cells were washed 3 times with PBS, and added with 4% paraformaldehyde to fix at room temperature for 20 min. The 4% paraformaldehyde was sucked out and then the cells were carefully washed 3 times with PBS, a Hoechst 33258 staining solution was added to stain at a temperature of 37° C. for 30 min. After the staining solution was discarded, the cells were washed 3 times with PBS, and the morphology of the nuclei was observed under a fluorescence microscope. The experiment was repeated 3 times.

The PC-9 non-small cell lung cancer cells in logarithmic growth phase were taken. The experiment was divided into 4 groups: group A (normal control group), group B (concentration of single ERG group was 40 μM), and group C (concentration of single GEF group was 5 μM), and group D (concentration of ERG+GEF group was 40+5 μM), and other operations were the same as above.

Figure 34:
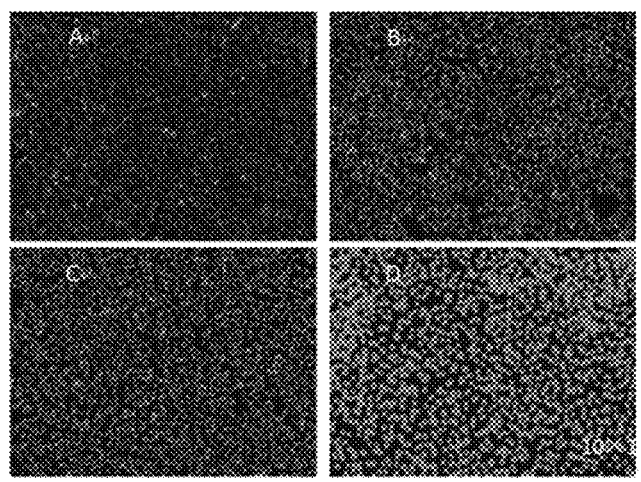
FIG. 34 shows nuclei of stained A549 cells acted by ERG and GEF.

The staining results of Hoechst 33258 for A549 cells are shown in FIG. 34. The A549 cells in the normal control group emitted uniform blue fluorescence, and there were only a few apoptotic cells; while the apoptotic cells in the administration groups showed more nuclear hyperchromasia and fragmentation, and emitted stronger fluorescence at the same time. ERG (20 μM) combined with GEF (20 μM) showed significantly more hyperchromatic apoptotic-like cells than single use of either, and the fluorescence emitted was stronger than the single group.

Figure 35:
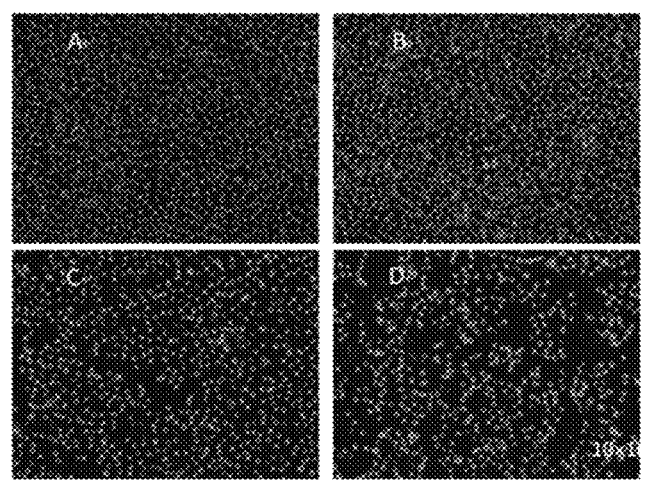
FIG. 35 shows nuclei of stained PC-9 cells acted by ERG and GEF.

The staining results of Hoechst 33258 for PC-9 cells are shown in FIG. 35. PC-9 cells in the normal control group emitted uniform blue fluorescence, there were no obvious morphological changes in nuclei, and there were only a few apoptotic cells; while the apoptotic cells in the experimental group showed nuclear hyperchromasia and fragmentation, and emitted stronger fluorescence. The amount of cells in the GEF group and the ERG+GEF group was significantly smaller than that in the blank group and the ERG group, indicating that the PC-9 cells die during the PBS washing process and cannot adhere to the wall, resulting in a decrease in cells observed under the microscope. ERG (40 μM) combined with GEF (5 μM) showed significantly more hyperchromatic apoptotic-like cells than single use of either, and the fluorescence emitted was stronger than the single group.

(VI) Research on Apoptosis and Cell Cycle of A549 Cells and PC-9 Cells after Administrating ERG and GEF by Flow Cytometry 1 Measurement of Apoptotic Rate Apoptosis in each group was detected by Annexin V-PI double staining flow cytometry. The number of A549 cells in logarithmic growth phase was adjusted to $1.5 \times 10^5 \cdot mL^{-1}$. After centrifuging at 800 rpm·min$^{-1}$ for 5 min, a single cell suspension was formed by blowing, beating and mixing well, 2 mL of an administration medium was added to each well in a 6-well culture plate, and 3 replicate wells were arranged for each concentration of each drug, ERG (10, 20, 40 μM), GEF (10, 20, 40 μM), and ERG+GEF (10+10, 20+20, 40+40 μM). The cells were cultured in a 37° C. 5% $CO_2$ incubator until 80% of the cells were fused and then a drug was added for treatment. After 48 h, a supernatant and cells were collected, washed 3 times with PBS, centrifuged at 800 rpm·min$^{-1}$ for 5 min, and resuspended with 100 μL of a 1× flow buffer, 5 μL of FITC and 5 μL of a PI fluorochrome were added to each administration well, and incubated for 15 min in the dark at room temperature, 400 μL of the 1× flow buffer was continuously added to each well and mixed uniformly at low speed with a vortex mixer, after the cells passed through a 400-mesh screen, the apoptotic rate was detected by flow cytometry within 1 h. The experiment was repeated 3 times.

PC-9 cells in logarithmic growth phase were taken, and 3 replicate wells were arranged for each concentration of each drug, ERG (20, 40, 80 μM), GEF (2.5, 5, 10 μM), and ERG+GEF (20+2.5, 40+5, 80+10 μM). Other operations were the same as above.

Figure 36:
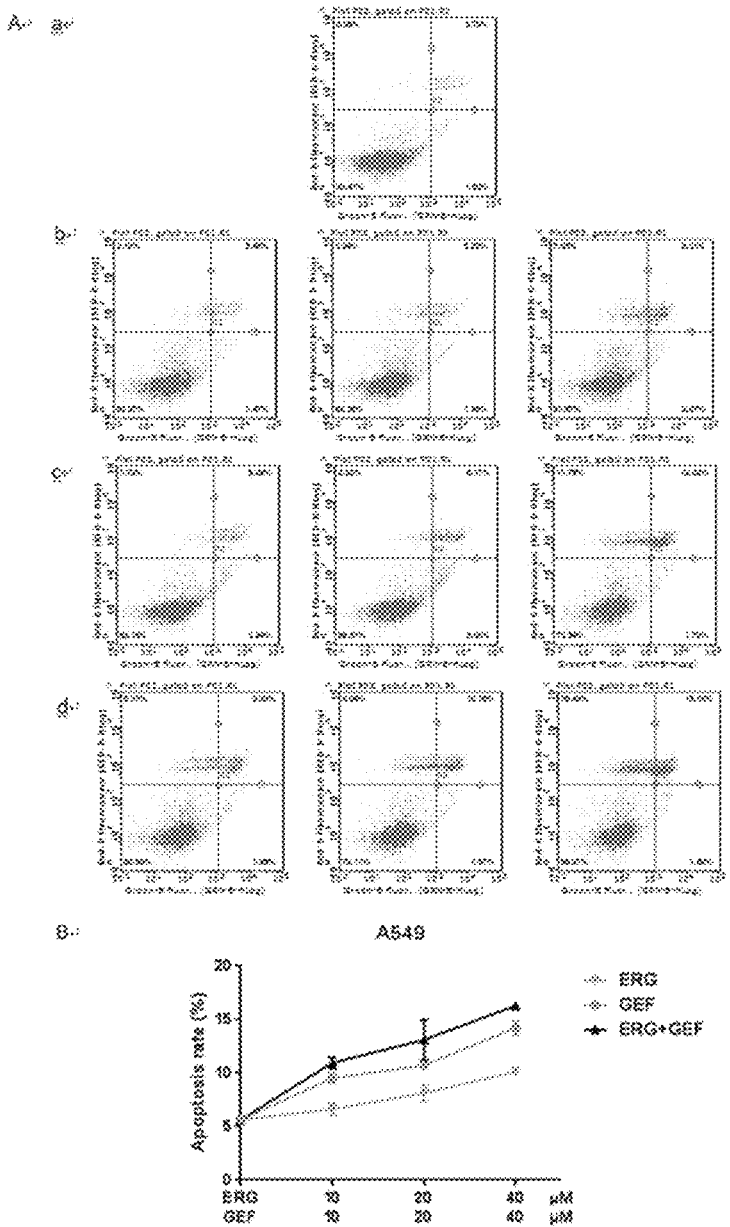
FIG. 36 shows apoptosis of A549 cells acted by ERG and GEF.

The flow results of A549 cell apoptosis are shown in FIG. 36 and FIG. 7. The apoptotic rate of the GEF group was higher than that of the ERG group at each concentration, and the apoptotic rates of the ERG+GEF (20+20 μM) group and the GEF (20 μM) were different (P<0.1), but the difference was not significant (P>0.05). The apoptotic rate of the ERG+GEF group was significantly higher than that of the single group (P<0.01), the concentrations of ERG and GEF were 40 and 40 μM, respectively, and the apoptotic rate was the highest, reaching 16.31±0.28%.

Figure 37:
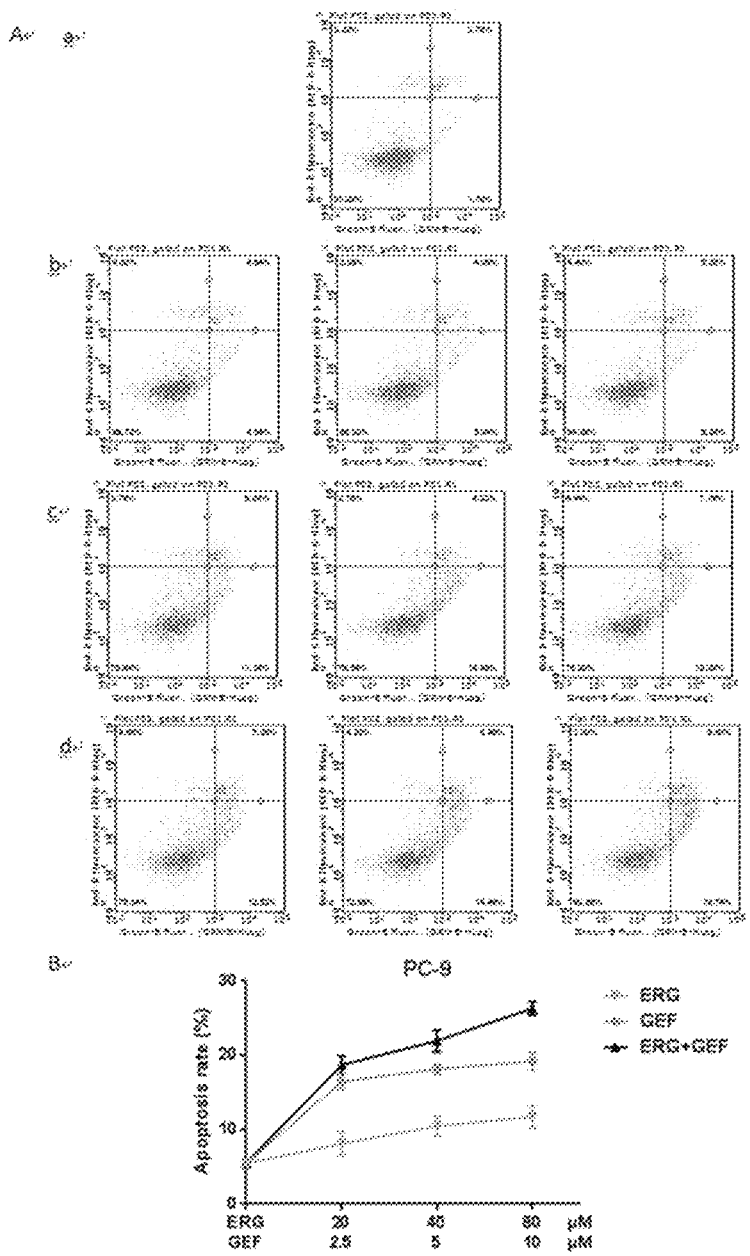
FIG. 37 shows apoptosis of PC-9 cells acted by ERG and GEF.

The flow results of PC-9 cell apoptosis are shown in FIG. 37 and FIG. 8. The apoptotic rate of the GEF group was higher than that of the ERG group at each concentration, and the apoptotic rates of the ERG+GEF (20+2.5 μM) group and the GEF (2.5 μM) were different (P<0.1), but the difference was not significant (P>0.05). The apoptotic rate of the ERG+GEF group was significantly higher than that of the single group (P<0.01), the concentrations of ERG and GEF were 80 and 10 μM, respectively, and the apoptotic rate was the highest, reaching 26.29±0.91%.

As shown in FIG. 8, by comparing the ERG (80 μg·mL$^{-1}$) and GEF (10 μg·mL$^{-1}$) groups with the ERG+GEF group (80+10 μg·mL$^{-1}$), **P<0.01, the difference was highly significant; by comparing the ERG (40 μg·mL$^{-1}$) and GEF (5 μg·mL$^{-1}$) groups and the ERG+GEF group (40+5 μg·mL$^{-1}$),##P<0.01, the difference was highly significant; by comparing the ERG (20 μg·mL$^{-1}$) group with the ERG+GEF group (20+2.5 μg·mL$^{-1}$), ^^P<0.01, the difference was highly significant; and by comparing the GEF (2.5 μg·mL$^{-1}$) group with the ERG+GEF group (20+2.5 μg·mL$^{-1}$), 0.05<P<0.1, there was a difference.

2 Measurement of Cell Cycle

The number of cells in logarithmic growth phase was adjusted to $1.5 \times 10^5 \cdot mL^{-1}$, the cells were inoculated into a 6-well culture plate, and cultured in a 37° C. 5% $CO_2$ incubator until 80% of the cells were fused and then a drug was added for treatment. The ERG (40 μM) group, GEF (40 M) group, and ERG+GEF (40+40 μM) group were set. After the drug acted for 48 h, a supernatant and cells were collected, centrifuged at 800 rpm·min$^{-1}$ for 10 min, washed once with PBS and fixed overnight with 75% ice ethanol, ethanol was discarded by centrifuging, and the cells were washed twice with PBS. The PBS was discarded, each sample was added with 0.5 ml of a PI staining solution to stain for 15 min at room temperature in the dark, and placed on a flow cytometer for measuring the proportion of cells in each cycle. The experiment was repeated 3 times.

PC-9 cells in logarithmic growth phase were taken, and 3 replicate wells were arranged for each concentration of each drug, ERG (40 μM), GEF (5 μM), and ERG+GEF (40+5 μM). Other operations were the same as above.

Figure 38:
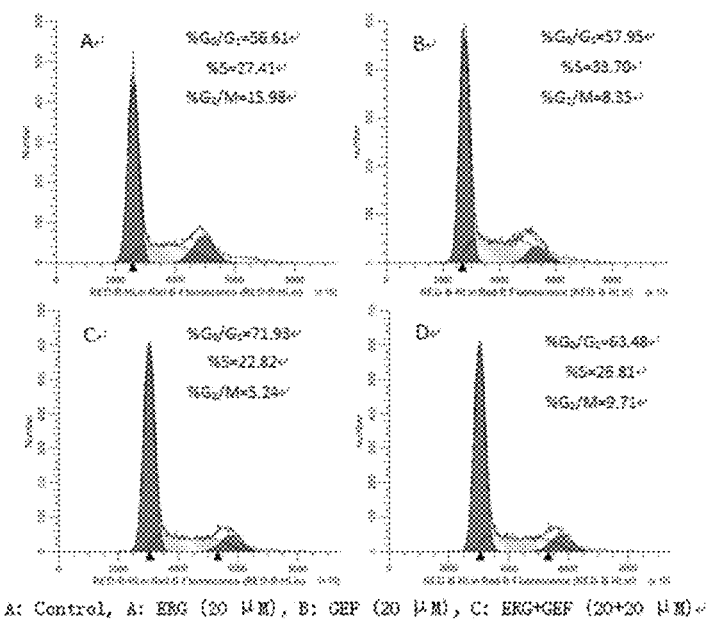
FIG. 38 shows the cell cycle of A549 cells acted by ERG and GEF.

The flow results of A549 cell cycle are shown in FIG. 38 and FIG. 9. When the ERG concentration was 20 μM, S phase arrest (32.05±2.27%) was generated in A549 cells, and there was a highly significant difference (P<0.01) compared with the S phase (29.63±2.15%) of the control group. GEF (20 μM) will generate significant G0/G1 phase (72.60±0.81%) arrest (P<0.01). After the combination of two drugs, the S phase fraction in the cell cycle will be increased under the action of ERG, so the G0/G1 phase fraction of A549 cells was lower than that of the GEF administration group (P<0.01), and there was a highly significant difference (P<0.01) compared with the G0/G1 phase (56.65±0.13) of the control group.

As shown in FIG. 9, compared with the Control group, *P<0.05, the difference was significant, and **P<0.01, the difference was highly significant.

Figure 39:
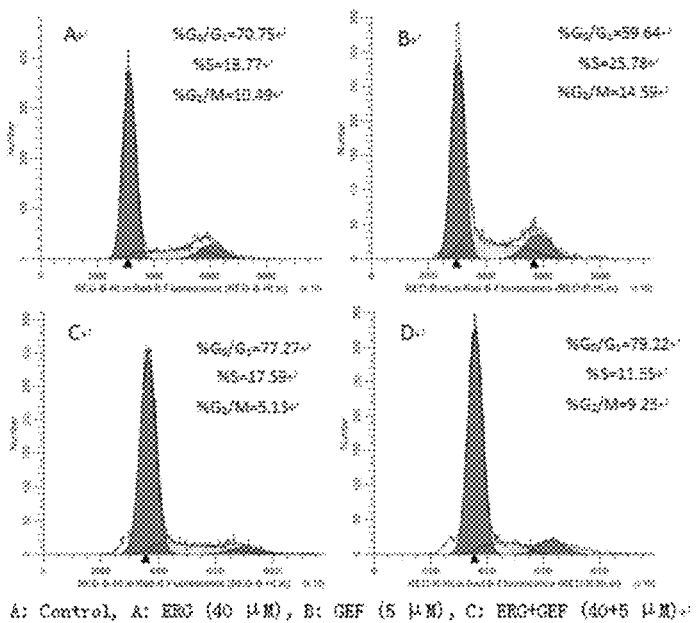
FIG. 39 shows the cell cycle of PC-9 cells acted by ERG and GEF.

The flow results of PC-9 cell cycle are shown in FIG. 39 and FIG. 10. When the ERG concentration was 40 μM, significant S phase arrest was generated in the PC-9 cell cycle, the S phase fraction was 26.93±2.02%, and there was a highly significant difference (P<0.01) compared with the S phase (19.13±1.20%) of the control group; meanwhile, certain G2/M phase arrest was also generated, the G2/M phase fraction was 13.58±1.80%, and there was a significant difference (P<0.05) compared with the G2/M phase (9.64±1.25%) of the control group. The 5 μM GEF could arrest cells in G0/G1 phase, the fraction was 78.35±1.58%, and there was a highly significant difference (P<0.01) compared with the G0/G1 phase (71.23±0.44%) of the control group. When the two drugs were combined, the G0/G1 phase fraction of PC-9 cells was 78.91±1.86% (P<0.01), and the S phase fraction was 13.18±3.16% (P<0.05). This suggests that the combination of the two drugs can not only increase the G0/G1 phase arrest to a certain extent, but also reduce the S phase fraction of the cell cycle.

As shown in Tables 1 to 10. Compared with the Control group, *P<0.05, the difference was significant, and **P <0.01, the difference was highly significant.

(VII) Expressions of AKT, p-AKT, EGFR, and p-EGFR after Administrating ERG and GEF by Western-Blots Assay The number of cells in logarithmic growth phase was adjusted to $2 \times 10^5 \cdot mL^{-1}$, the cells were inoculated into a 6-well culture plate, and after the drug was added for treating for 48 h, the total proteins of cells were extracted, and the concentration thereof was measured by a BCA kit. After the total protein concentrations of all groups were adjusted to the same, a protein sample and a 5× loading buffer were mixed and then boiled for 5 min at a temperature of 100° C., added to the corresponding concentration of SDS-PAGE gel to conduct electrophoresis until the bromophenol blue is 1 cm away from the bottom of the gel, and then transferred onto a 0.22 μm PVDF membrane, and blocked with a Western blocking solution for 1 h. After slightly washing, an appropriate amount of primary antibody AKT (1:1000), p-AKT (1:500), EGFR (1:1000), p-EGFR (1:500), and β-actin (1:4000) were respectively added and incubated overnight at a temperature of 4° C., and rinsed with a Western washing solution 3 times for 5 min each time; the corresponding source of fluorescent secondary antibody was added and incubated for 2 h at room temperature, rinsed with the Western washing solution 3 times for 5 min each time, the membrane was scanned by an Odyssey infrared fluorescence scanning imaging system, and the band gray value was calculated by Image J software for quantitative analysis. The experiment was repeated 3 times.

A549 cells in logarithmic growth phase were taken, and other operations were the same as above.

Figure 40:
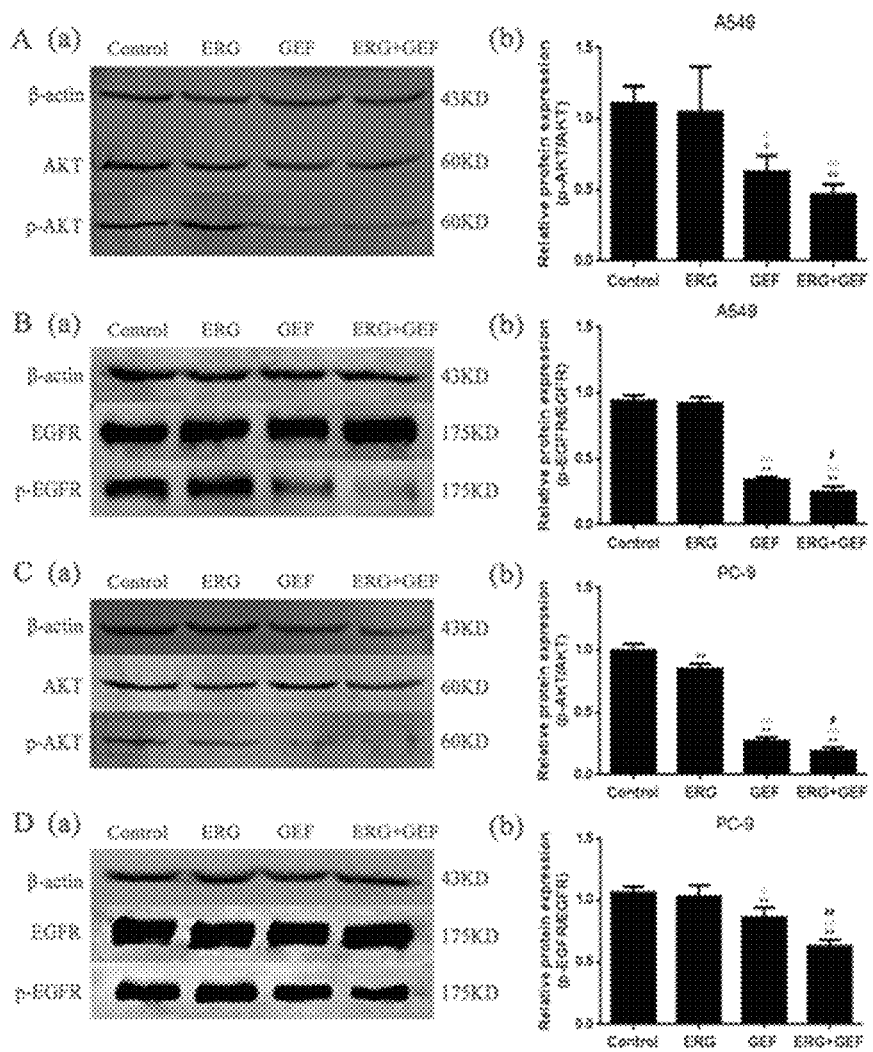
FIG. 40 shows the protein expression and quantitative analysis of A549 and PC-9 cells administrated with ERG and GEF.

The protein expression results are shown in FIG. 40. The expression levels of phosphorylated proteins in the administration groups were all decreased to a certain extent, wherein the effect was the most obvious when the two drugs were combined, indicating that the combination of ERG and GEF can inhibit the expression of EGFR and AKT-related signal pathways to a certain extent. In A549 cells, the p-AKT/AKT levels and p-EGFR/EGFR levels were significantly decreased in the GEF group and the ERG+GEF group compared with the blank control group and the ERG group (P<0.05 and P<0.01). The p-EGFR/EGFR level was significantly decreased in the ERG+GEF group compared with the GEF group (P<0.05). In PC-9 cells, compared with the blank control group, the p-AKT/AKT levels were significantly increased in other administration groups (P<0.01), and the p-EGFR/EGFR levels in the GEF group and the ERG+GEF group were significantly decreased (P<0.01). Compared with the ERG group, the p-AKT/AKT levels and p-EGFR/EGFR levels in the GEF group and the ERG+GEF group were significantly decreased (P<0.05 and P<0.01). Compared with the GEF group, the p-AKT/AKT level and p-EGFR/EGFR level were significantly decreased in the ERG+GEF group (P<0.05 and P<0.01). β-actin was used as an internal reference protein in the experiment.

As shown in FIG. 40, compared with the Control group, *P<0.05, the difference was significant, and **P<0.01, the difference was highly significant; compared with the ERG group, $^{\Delta}$P<0.05, the difference was significant, and $^{\Delta\Delta}$P<0.01, the difference was highly significant; compared with the GEF group, $^{\#}$P<0.05, the difference was significant, and $^{\#\#}$P<0.01, the difference was highly significant.

III. Analysis and Discussions

The research results show that the ERG group, the GEF group and the two-drug combination group have certain inhibitory effects on proliferation of A549 and PC-9 cells, showing certain concentration dependence. When apoptosis was detected by the flow cytometer, it was found that the apoptotic rate of PC-9 cells was much higher than that in A549 cells when ERG and GEF were combined. The possible cause was as follows: GEF was sensitive to PC-9 cells and not sensitive to A549 cells. The main pathway by which ERG causes cell death might not be the apoptotic pathway. In the cell cycle test, the S phase cell fraction was significantly increased in the ERG group compared with the control group (P<0.01), and the ERG+GEF group could cause the G0/G1 phase arrest of the two cells to inhibit the proliferation thereof, thereby inhibiting the further development and deterioration of tumors.

In the Western-blots test, the p-AKT/AKT level and p-EGFR/EGFR level in the ERG+GEF group were significantly decreased (P<0.01), indicating that the combination of the two drugs could inhibit the expression of EGFR signal pathway to a certain extent. While the PI3K/AKT/mTOR signal pathway is the downstream signal pathway of the EGFR signal pathway, we can speculate whether the combination of the two drugs can inhibit the expression of the PI3K/AKT/mTOR signal pathway to a certain extent, thereby causing apoptosis of tumor cells.

IV. Conclusions

It was proved to a certain extent that the combination of ERG and GEF had synergistic and sensitizing effects on GEF-sensitive PC-9 cells, and can increase the sensitivity of GEF-resistant A549 cells. In recent years, many studies have shown that the PI3K/AKT/mTOR signal pathway plays an important role in tumor cells. Therefore, the more comprehensive anti-tumor molecular mechanism of combination of ERG and GEF needs to be further studied.

Figure 41:
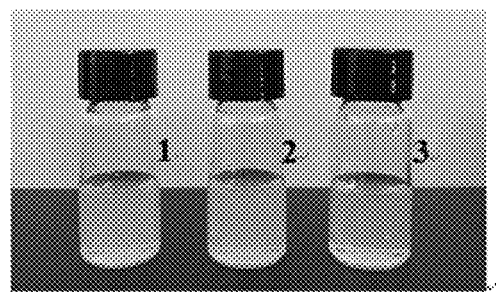
FIG. 41 shows the appearance of each liposome.
Figure 42:
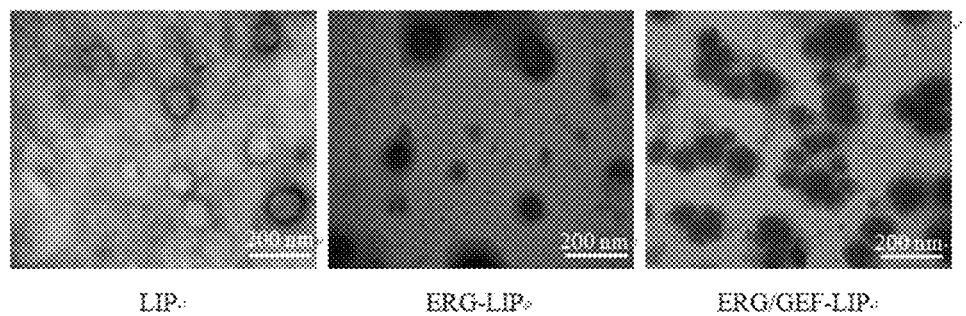
FIG. 42 shows a transmission electron micrograph of each liposome.
Figure 43:
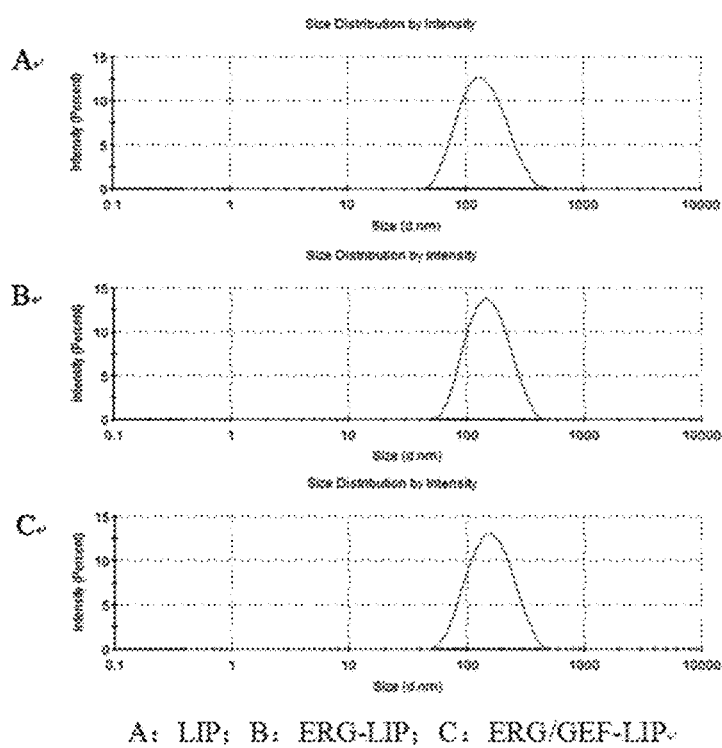
FIG. 43 shows distribution of changes in particle size of each liposome.
Figure 44:
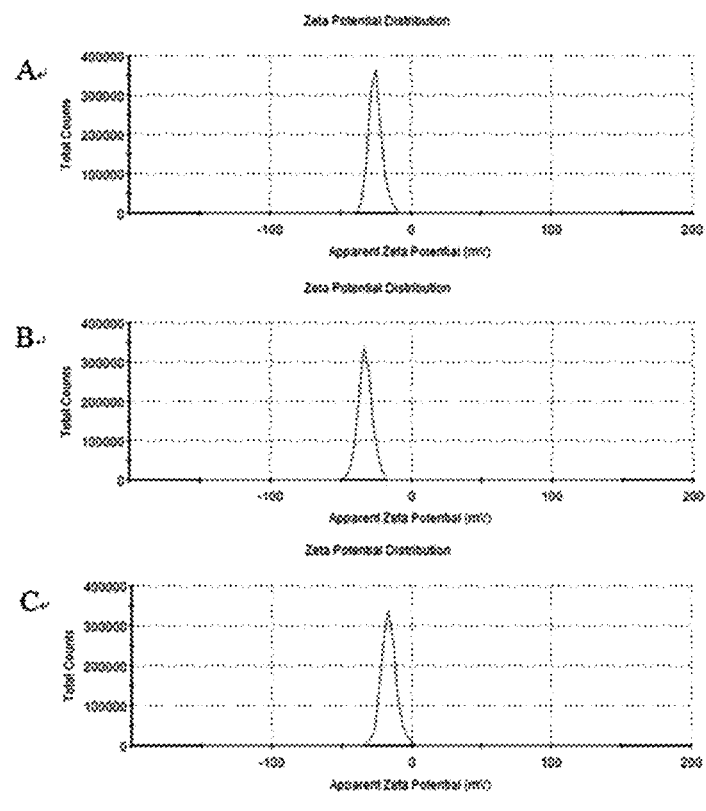
FIG. 44 shows a Zeta potential of each liposome.

ERG/GEF-LIP Quality Evaluation 1.1 Morphological Observation
1.1.1 Appearance Morphology
LIP, ERG-LIP, and ERG/GEF-LIP solutions are milky white and uniform in color, as shown in FIG. 41.
1.1.2 Microscopic morphology (observing liposomes by transmission electron microscope)
Samples were prepared by negative staining. At room temperature, LIP, ERG-LIP, and ERG/GEF-LIP samples were taken, and dropped onto a special copper mesh of an electron microscope, excess samples were blotted up with filter paper, and the samples were kept stand for 1 min, and then negatively stained with 1% phosphotungstic acid, and after keeping stand for 30 s, the excess staining solution of the copper mesh was sucked up by filter paper, and then the samples were naturally dried and observed and photographed by the electron microscopy. The transmission electron microscopy results show that the liposomes were round in morphology and uniform in particle size distribution (FIG. 42).
1.2 Particle Size and Distribution Thereof
LIP, ERG-LIP, ERG/GEF-LIP samples were taken, and diluted 20 times with pure water, and the average particle size and the distribution thereof were measured by a laser particle size analyzer. The results are shown in FIG. 43. The results show that the average particle size of LIP is 131.4±2.3 nm, the polydispersity index PDI is 0.176±0.002 and less than 0.3, the average particle size of ERG-LIP is 139.0±2.8 nm, PDI is 0.203±0.016 and less than 0.3, the average particle size of ERG/GEF-LIP is 142.5±1.0 nm, PDI is 0.199±0.036 and less than 0.3, and the particle size distribution of liposomes in each group is more centralized.
1.3 Measurement of Zeta Potential
LIP, ERG-LIP, ERG/GEF-LIP samples were taken, and diluted 20 times with pure water, and the potential was measured by a Zeta potentiometer. The results are shown in FIG. 44. The results show that the Zeta potential of LIP is −25.7±0.7 mV, the Zeta potential of ERG-LIP is −33.3±0.6 mV, the Zeta potential of ERG/GEF-LIP is −19.0±3.1 mV, and the liposomes are negatively charged.
1.4 Measurement of pH
Three batches of ERG/GEF-LIP samples were taken at room temperature, and diluted to a certain concentration, and the pH value was measured with a pH meter. The average pH value of the three batches of samples was 5.05±0.12 by measurement.
1.5 Measurement of Peroxide Values (POV) of Liposomes
In the experiment, the degree of oxidation of liposomes was investigated by malondialdehyde assay, wherein a TTH test solution was prepared by adding 200 mL of 0.25 mol·L$^{-1}$ hydrochloric acid to 0.75 g of 2-thiobarbituric acid and 30 g of trichloroacetic acid, warming to dissolve, and filtering after cooling. 1 mL of ERG/GEF-LIP was accurately weighed and placed in a 10 mL centrifuge tube and added with 5 mL of prepared TTH reagent. After mixing well, a mixture was heated at a temperature of 100° C. for half an hour. A supernatant was sucked up, and the TTH test solution was used as a blank control. The absorbance value was measured at a wavelength of 535 nm and recorded as a peroxide value. Three batches of samples were measured in parallel, and the average peroxide value was 0.0237±0.0018.

Figure 45:
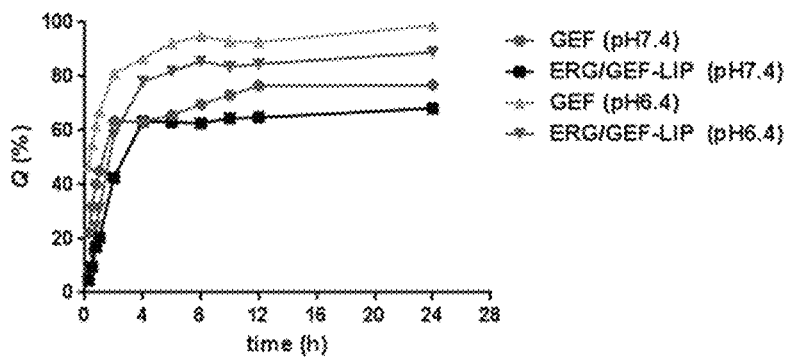
FIG. 45 shows cumulative release rates of GEF and ERG/GEF-LIP in different pH release media.

1.6 Entrapment Efficiency and Drug Loading Capacity
Three batches of ERG/GEF-LIP samples were taken, wherein the average entrapment efficiency of GEF was 96.49±1.00%, and the drug loading capacity was 5.73±0.62%. The average entrapment efficiency of ERG was 95.33±0.21%, and the drug loading capacity was 3.94±0.10%.
1.7 Release Rate
Due to its high lipid solubility, ERG could be dissolved in pure methanol or pure ethanol. However, the membranes of the liposomes directly ruptured in pure methanol or pure ethanol, and a release medium was difficult to meet the "sink" condition of ERG. Therefore, the in vitro release of ERG was not investigated in the experiment. While GEF was used as a weakly basic drug, its solubility has pH dependence. Therefore, the in vitro release of GEF drug under different pH conditions was investigated in the experiment. 4 mL of ERG/GEF-LIP and 4 mL of a GEF citric acid solution were accurately and respectively absorbed, and placed in dialysis bags, the dialysis bags were tightly clamped with dialysis clamps, put into 100 mL of pH 7.4 and pH 6.4 40% methanol-containing phosphate buffers, and placed in a constant temperature water bath oscillator (shaking rate: 100 rpm·min$^{-1}$, and release temperature: 37° C.), 1 mL of a dialysate was sucked up respectively at 0.25, 0.5, 0.75, 1, 2, 4, 6, 8, 10, 12, and 24 h, and 1 mL of a fresh dialysis medium was replenished. Each sample was filtered through a 0.45 μm microporous membrane, samples were injected by HPLC, the peak areas were measured, and substituted into the linear regression equation to calculate the drug release concentration of GEF at each sampling point, which was recorded as $c_1$, and the total dose of GEF was recorded as $M_0$. Calculation was carried out according to the following formula:

$$\text{Cumulative release percentage } Q\ (\%) = (c_1 \times V_0 + \Sigma_{n=1}^{t-1} Cv)/M_0 \times 100\%$$

where $c_1$ is the release concentration of GEF in each sampling point, $V_0$ is the volume of a release medium, V is the sampling volume, and $M_0$ is the total dose of GEF.
The results from FIG. 45 indicate that the in vitro release of GEF has significant pH dependence. In the pH 7.4 40% methanol-containing phosphate buffer, the cumulative release percentage of a GEF raw medicine within 24 h was 76.91%, and the cumulative release percentage of ERG/GEF-LIP was 68.26%. In the pH 6.4 40% methanol-containing phosphate buffer, the cumulative release percentage of the GEF raw medicine within 24 h was 98.91%, and the GEF raw medicine was almost completely released. The cumulative release percentage of ERG/GEF-LIP within 0.5 h was 14.25%<40%, and the cumulative release percentage of ERG/GEF-LIP within 6 h was 81.97%>80%, and the cumulative release percentage of ERG/GEF-LIP was 88.92% until 24 h. The requirements for the liposome burst effect in the *Chinese Pharmacopoeia* 2015 edition are as follows: the release amount within 0.5 h at the beginning should be ≤40% [49], and the cumulative release percentage within 24 h exceeds 80%. RG/GEF-LIP meets the requirements in the condition that the pH 6.4 40% methanol-containing phosphate buffer served as the release medium. Drug-loaded liposomes were more readily released in a weakly acidic environment, which will be favorable for the liposomes to selectively release the contents in the tumor acidic environment.
The fitting of a drug release process using a certain model is a common method for research on a drug release mechanism, mainly including a zero-order model, a first-order model, Higuchi model and so on. The in vitro cumulative release percentages of the GEF solution and ERG/GEF-LIP were fitted according to the zero-order, first-order and Higuchi equations respectively. The model formula is shown in FIG. 11. The fitting results and correlation coefficients are shown in FIG. 12.

The fitting results in FIG. 12 show that the in vitro release of the GEF citric acid solution is closer to the Higuchi equation in the pH 7.4 release medium, but the fitting correlation coefficient of the first-order kinetic equation also reaches 0.9952. The in vitro release of the GEF citric acid solution conforms to the first-order kinetic equation in the pH 6.4 release medium. The in vitro release of ERG/GEF-LIP conforms to the first-order kinetic equation in different pH release media.

1.8 Induction and Measurement of Resistance Index (RI) of GEF-Resistant Strain in Non-Small Cell Lung Cancer Cells PC-9/GR[50] was constructed by an intermittent action method of stepwise increasing GEF concentration as follows: the PC-9 cells in logarithmic growth phase were inoculated into a 1640 medium containing 10% FBS, a GEF solution having a concentration of 10 μM was used to act for 48 h and then the drug-containing medium was discarded, and the culture was continued after a fresh medium was added. After waiting for PC-9 to resume the normal growth rate, the cells were treated with the GEF with a concentration of 10 μM for 48 h after digestion and passage. The above operation was repeated, and the cells were intermittently induced for about 3 to 4 weeks, and named PC-9/GR.

Figure 46:
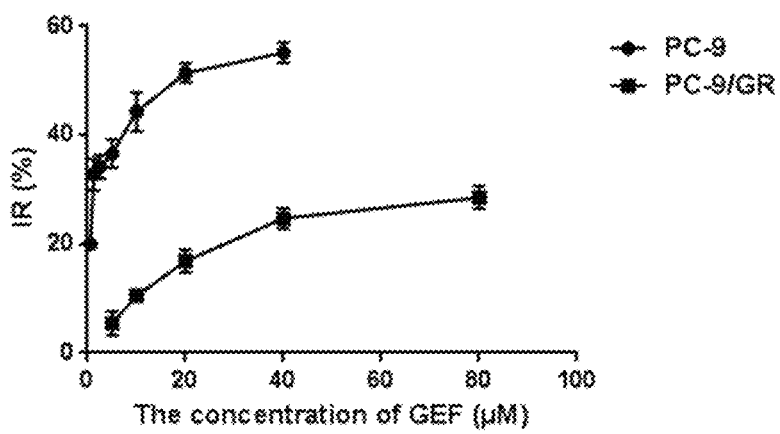
FIG. 46 shows the inhibitory effects of GEF on proliferation of sensitive cells and drug-resistant cells.

The PC-9/GR and PC-9 cells in logarithmic growth phase were taken, and adjusted to $5 \times 10^4 \cdot mL^{-1}$ after trypsinization. 100 μL of cells was added to each well, inoculated in a 96-well culture plate and cultured in a 37° C. 5% $CO_2$ incubator. When the cells were grown to about 80%, GEF was respectively added according to the concentration gradient. 5 replicate wells were arranged in each group, and a normal control group was set at the same time. MTT assay was performed 24 hours after administration. For the specific MTT operation, please refer to "(IV) Research on inhibitory effects of ERG combined with GEF on proliferation of A549 and PC-9 cells (MTT test)" in Part I in details. In the experiment, measurement was performed in parallel three times, and the results are shown in FIG. 46 and FIG. 13. The results show that the inhibitory rates of different GEF on the PC-9 cells were significantly higher than that on PC-9/GR cells (P<0.01). The PC-9/GR cell resistance index was 13.90, which was analyzed by SPSS17.0 software, and the cells were highly resistant to drugs.

Inhibitory $rate IR$ (%) =

$$\frac{Control\ groupOD - Experimental\ groupOD}{Control\ groupOD} \times 100\%$$

Figure 47:
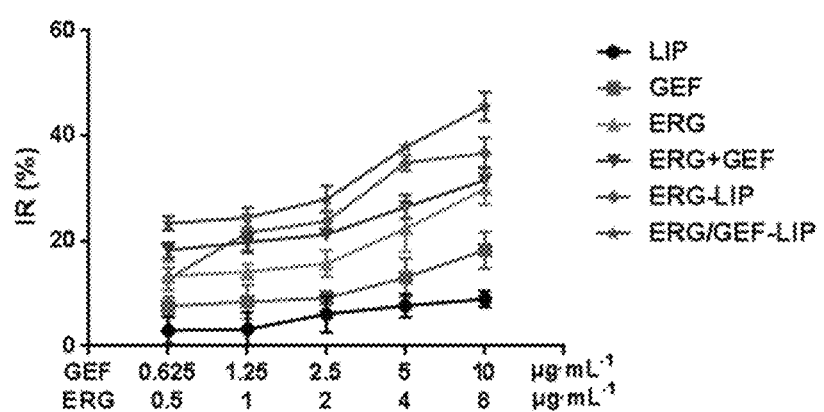
FIG. 47 shows 24 hMTT test results of raw medicines and liposomes.

Resistance index $RI$ = Resistant cell $IC50$/Parent cell $IC50$ 1.9 Inhibition Test of ERG/GEF-LIP on Proliferation of Resistant Cells in vitro PC-9/GR cells were cultured in vitro, and administrated with ERG, GEF, ERG+GEF, a blank liposome (LIP), ERG-LIP, and ERG/GEF-LIP to stimulate for 24 h, and then the cell proliferation inhibitory rates after administrating different concentrations of drugs were measured. For the specific MTT operation, please refer to "(IV) Research on inhibitory effects of ERG combined with GEF on proliferation of A549 and PC-9 cells (MTT test)" in Part I in details. In the experiment, measurement was performed in parallel three times, and the results are shown in FIG. 47. When the drug acted for 24 h, the inhibitory rate at each concentration in the LIP group was less than 10%, indicating that the excipient has no inhibitory effect on drug-resistant cells within this concentration range. At the same administration concentration, the inhibitory rate of the ERG/GEF-LIP group was significantly higher than that of other groups, and the difference was highly significant (P<0.01). Among them, the inhibitory rate of the GEF group was the lowest except for the LIP group, which also proves that a drug-resistant cell model is successfully established to a certain extent. The whole experiment results show that after ERG and GEF are prepared into liposomes, the inhibitory effects on proliferation of PC-9/GR cells in vitro can be significantly increased.

1.10 In Vitro Drug-Resistant Cell Uptake Test of ERG/GEF-LIP

Figure 48:
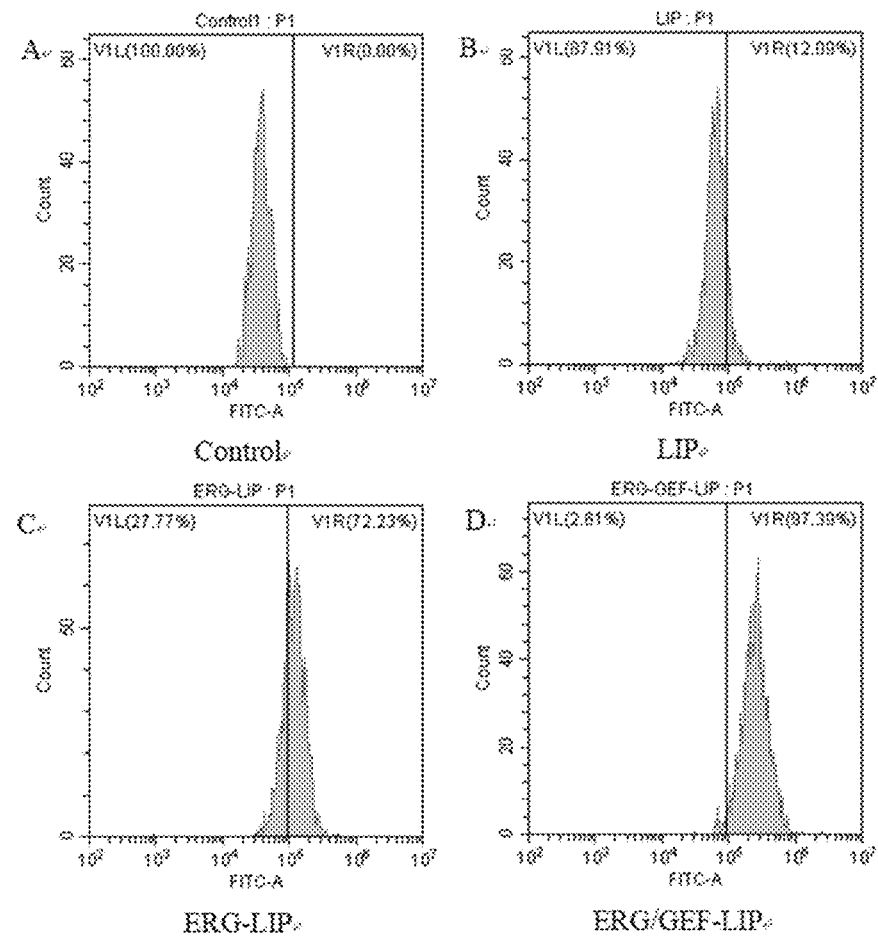
FIG. 48 shows flow cytometry uptake diagrams of ERG/GEF-LIP.

An FITC methanol solution was subjected to rotary evaporation together with SPC, Chole and ERG to form a film. The concentration of FITC in LIP and ERG-LIP was 275 $\mu g \cdot mL^{-1}$, and the concentration of FITC in ERG/GEF-LIP was 137.5 $\mu g \cdot mL^{-1}$. The prepared FITC-labeled LIP, ERG-LIP, and ERG/GEF-LIP were quantitatively diluted with the complete 1640 medium until the final concentration of FITC was 25 $\mu g \cdot mL^{-1}$. PC-9/GR cells were inoculated in a 6-well plate, and when the cells were grown to 80%, the medium was discarded, and the cells were added to each liposome administration group containing FITC with a final concentration of 25 $\mu g \cdot mL^{-1}$. After incubating for 2 h in an incubator, the drug was discarded, the cells were washed 3 times with PBS, and the cells were collected by trypsinization, added with PBS to be washed 3 times, centrifuged to remove a supernatant, and then resuspended by adding 0.5 mL of PBS, and the uptake intensity of the cells in different liposome administration groups were detected by the flow cytometer. The results are shown in FIG. 14 and FIG. 48. The experimental results show that compared with the normal control group, the uptake intensity of the ERG/GEF-LIP group is the highest (P<0.01), reaching 97.14±0.93%, followed by the uptake rate of the ERG-LIP group, reaching 73.25±0.95%, indicating that the double drug-loaded liposome has the best cellular uptake effect compared with the single drug-loaded liposome, and the drug can enter the interior of the cell more smoothly to play a pharmacodynamic role through a liposome carrier. The uptake rate of the LIP group was only 13.81±1.78%, indicating that the unloaded liposomes have no much effect on cellular uptake.

III. Analysis and Discussions

In the experiment in this part, on the basis of ERG-LIP, GEF was entrapped by the ammonium sulfate gradient method to prepare ERG/GEF-LIP. By using the GEF entrapment rate as an index, through the response surface design, the four factors: incubation time, incubation temperature, ammonium sulfate concentration and gefitinib concentration were optimized and analyzed to determine the best prescription and process for entrapping GEF by the ammonium sulfate gradient method as follows: the incubation temperature was 40° C., the incubation time was 50.35 min, the GEF concentration was 0.22 $mg \cdot mL^{-1}$, and the ammonium sulfate concentration was 195.81 mM. The resulting ERG/GEF-LIP was a negatively charged liposome.

It was found by investigating the in vitro release rate that the solubility of GEF as a weakly basic drug had pH dependence [51-52]. In the pH 7.4 phosphate buffer, white turbidity appeared in the liposome, and almost no free GEF was detected by HPLC. In the pH 6.4 release medium, the cumulative release percentage within 24 h was greater than 80%, which meets the requirements of the National Pharmacopoeia 2015 edition. The in vitro drug-resistant cell test shows that the blank liposome has no toxic effect on the drug-resistant cells themselves. ERG/GEF-LIP increased the sensitivity of PC-9/GR cells to a certain extent, and its proliferation inhibitory effect was the best.

IV. Conclusions

In this part, ERG and GEF were successfully co-loaded in the liposome, and the entrapment efficiency was greater than 90%. The in vitro drug-resistant cell test confirms that ERG/GEF-LIP has a stronger tumor cell proliferation inhibitory effect and a stronger cellular uptake effect.

Preparation and Quality Evaluation of RGD Cyclic Peptide/R8 Peptide Modified ERG-GEF Combined Compound Liposome Freeze-Dried Powder In this part, DSPE-PEG$_{3400}$-c(RGDfk) and DSPE-PEG$_{1000}$-R8 were inserted into the lipid membrane of ERG/GEF-LIP by the post-insertion method to prepare RGD cyclic peptide/R8 peptide modified ERG/GEF-LIP(RGD/R8-ERG/GEF-LIP). Considering the stability of the liposome itself, it was prepared into a freeze-dried powder form, and its morphology, particle size distribution, Zeta potential, serological stability, and in vitro release were preliminarily investigated. A preliminary study on anti-lung cancer in vitro was conducted against the drug-resistant cells PC-9/GR.

I. Experimental Materials

Human lung cancer PC-9/GR cells were constructed by an intermittent action method of stepwise increasing GEF concentration in human lung cancer PC-9 cells.

II. Methods and Results (1) Synthesis of RGD Cyclic Peptide and R8 Peptide

DSPE-PEG3400-COOH and DSPE-PEG1000-COOH raw medicines were purchased from Xi'an Ruixi Biological Technology Co., Ltd., and were submitted to Qiangyao Biological Technology Co., Ltd. to synthesize a DSPE-PEG3400-c(RGDfk) peptide and a DSPE-PEG1000-R8 peptide. After the DSPE-PEG3400-c(RGDfk) and DSPE-PEG1000-R8 were purified, the molecular weights were identified to be 4751.8 and 3015.6 respectively by MALDI-TOF-MS and H-NMR analysis.

(II) Preparation of RGD/R8-ERG/GEF-LIP

ERG/GEF-LIP was prepared first and then preparation was performed by the post-insertion method (incubate in a 55° C. water bath for 1 h). R8-ERG/GEF-LIP was prepared by accurately weighing SPC, Chole, and R8 peptide according to a molar ratio of 5:1:0.07; RGD-ERG/GEF-LIP was prepared by accurately weighing SPC, Chole, and RGD peptide according to a molar ratio of 5:1:0.07; and RGD/R8-ERG/GEF-LIP was prepared by accurately weighing SPC, Chole, R8 peptide and RGD peptide according to a molar ratio of 5:1:0.07:0.07. The FITC-labeled liposome, that is, the FITC methanol solution was added to the lipid material to subject to rotary evaporation together to form a film, and the final mass concentration of FITC in the uptake test was determined to be 25 µg·mL$^{-1}$ according to the preliminary investigation results of the laboratory.

(III) Preparation of RGD/R8-ERG/GEF-LIP Freeze-Dried Powder

The liposome suspension is prone to accumulation, fusion and drug leakage during storage, and the phospholipid has the characteristics of easy oxidation and hydrolysis, which is difficult to meet the long-term stability requirements of pharmaceuticals, so that the industrial production and clinical application thereof are greatly limited [56-58]. The interaction between the water-soluble drug and the liposome membrane was relatively weak, and the long-term stability problem is more prominent. In this chapter, the freeze-dried powder was prepared by the freeze-drying method, and the effects of the freeze-drying process and the type of freeze-drying protective agent on liposome morphology were investigated. On this basis, the effects of the addition amount of the freeze-drying protective agent on the appearance, morphology and entrapment efficiency of the liposome before and after freeze-drying were mainly investigated.

Since ERG/GEF-LIP and RGD/R8-ERG/GEF-LIP were prepared in this paper, the preparation cost of the target head modified liposome was too high, in the subsequent freeze-drying process investigation, in order to save the experimental cost, ERG/GEF-LIP was used to investigate and the best prescription and process were screened out and applied to RGD/R8-ERG/GEF-LIP for verification.

1 Preparation of Freeze-Dried Liposome

Ice crystals generated in the freeze-drying process caused damage to the liposome and caused the samples to be shapeless and produce shrinkage. In order to reduce its damage to the liposome and obtain a certain degree of aesthetics, it was generally necessary to add the freeze-drying protective agent [59]. The method in which the freeze-drying protective agent was added was divided into an internal addition method and an external addition method. The external addition method refers to the direct addition of the protective agent to the prepared liposome suspension, and the internal addition method refers to the addition of the protective agent to a liposome hydration medium (195.81 mM ammonium sulfate solution) for co-hydration. In this experiment, a 5% sucrose solution was used as the freeze-drying protective agent for the experiment. The results of FIG. 15 show that the particle size of the liposome obtained by the internal addition method is significantly higher than that of the liposome obtained by the external addition method ($P<0.01$), and the appearance of a freeze-dried finished product is obviously collapsed and shrunk. In order to save the experimental cost, the entrapment efficiency was not further measured. Based on the above experimental results, the external addition method was selected as the addition method of the freeze-drying protective agent in this paper.

2 Investigation of Freeze-Drying Process 2.1 Measurement of Eutectic Point of Freeze-Dried Powder The eutectic point of a material was the temperature at which the ice crystals inside the frozen material begin to melt when the temperature rises to a certain value. In order to ensure that the material did not erupt during the pumping and vacuumizing process and did not collapse and deform during the sublimation drying process, the eutectic point of a liquid drug needed to reach below 5 to 10° C. In the test, the prepared freeze-dried sample was placed in a cold trap, and the change values of the cold trap temperature and the sample temperature with time were recorded, and a cooling curve was drawn. The results are shown in FIG. 49.

Figure 49:
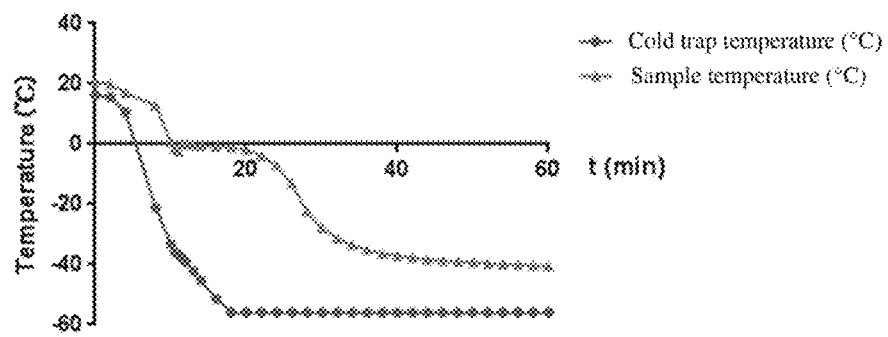
FIG. 49 shows cooling curves of a sample and a cold trap.

It can be seen from FIG. 49 that the sample temperature decreases with time from 0 to 11 min, and there is a short temperature rising process in 11 to 12 min, and the temperature rises from −2.3° C. to 0° C. at this time, indicating that the lowest eutectic point of the sample is between −3 and 1° C., so the heating temperature of a first stage (sublimation drying) should not exceed −3° C.

2.2 Investigation of Prefreezing Rate

Prefreezing rate is one of the important parameters in the freeze-drying process, which directly affects the freeze-drying effect of the sample. There are usually two methods: a quick-freezing method and a slow-freezing method, wherein the quick-freezing method includes: firstly starting the cooling function of freeze-drying equipment, so that the temperature of the cold trap portion is lowered to the minimum temperature (−56° C.), and then placing the prefrozen sample in the cold trap. The method is characterized in that the sample can be quickly cooled. The slow-freezing method includes: firstly placing the sample in the cold trap and then starting the cooling function of the equipment. The method is characterized in that the temperature of the sample itself is slowly decreased. Different prefreezing rates may cause osmotic pressure between the frozen outer phase layer and the molecular layer of the liposome, resulting in leakage of the drug from the liposome. Therefore, in the experiment, the slow-freezing method and the quick-freezing method were used for conducting the experiments respectively. The experimental results are shown in FIG. 16. The particle size of the liposome obtained by the slow-freezing method was significantly higher than that of the liposome obtained by the quick-freezing method (P<0.01), and the appearance of a freeze-dried finished product was slightly shrunk, which was not as fluffy as the quick-freezing method. Therefore, in the experiment, the quick-freezing method was adopted, that is, the temperature of the cold trap portion in the equipment was firstly lowered to the minimum temperature (−56° C.), and then the sample was placed in the cold trap. 2.3 Prefreezing time The length of prefreezing time determines whether the sample is completely frozen or not, which is a key factor affecting the quality of the freeze-dried product. In the experiment, the quality of the freeze-dried sample which was pre-frozen for 1, 2, 3, 4, 6 and 8 h in the cold trap by the quick-freezing method was investigated. Sublimation drying was performed according to the procedure (−25 to −15° C.: 300 min; −15 to −10° C.: 360 min; −10 to 0° C.: 300 min; 0 to 10° C.: 360 min; 10 to 20° C.: 300 min; 20 to 30° C.: 360 min). The results are shown in FIG. 17. The results show that when the prefreezing time reaches 4 h, the sample obtained is full in appearance and small in particle size change, and the ERG and GEF entrapment efficiency is little in change than that before freeze-drying. To save time and cost, the prefreezing time was determined to be 4 h.

2.4 Investigation of Freeze-Drying Time

The storage temperature of the freeze-dried powder must be lower than the glass transition temperature of the drug, otherwise the drug may have adverse symptoms such as collapse, surface shrinking, hardening and discoloration, and agglomeration. The water content of the freeze-dried powder is an important factor affecting the glass transition temperature. The higher the water content of the freeze-dried powder is, the lower the glass transition temperature is and the worse the stability of the freeze-dried powder is, so water is also an important factor for controlling the quality of the freeze-dried product. In the experiment, the water contents at freeze-drying times of 20, 25, 30, 35, 48, and 72 h were investigated respectively to determine the optimum freeze-drying time. The results are shown in FIG. 18. Finally, freeze-drying 48 h was used as the freeze-drying time.

3 Optimization of Freeze-Drying Prescription

An indispensable excipient in the freeze-drying process is a freeze-drying protective agent. The freeze-drying protective agent protects the integrity of a liposome membrane structure like a stent and prevents drug leakage. Addition of the freeze-drying protective agent prior to freeze-drying and controlling of appropriate cooling speed can reduce damage to the liposome caused by ice crystals during freezing. In the freeze-drying process, if the freeze-drying temperature was higher than the glass transition temperature of the drug, the viscosity of the drug was rapidly lowered, the microstructure was destroyed, the surface was shrunk, and finally collapse occurred. The main role of the freeze-drying protective agent in the liposome freeze-drying process was to increase the glass transition temperature of liposome and reduce the mechanical damage to liposome vesicles caused by ice crystals during freeze-drying.

Therefore, it is very important to choose a suitable freeze-drying protective agent. The commonly used freeze-drying protective agent includes sugars and alcohols such as glucose, sucrose, lactose, mannitol, sorbitol, xylitol, etc. In the experiment, glucose, sucrose, lactose, mannitol, sorbitol, and xylose were to be selected as the freeze-drying protective agent, and the protective effects thereof during liposome freeze-drying process were investigated.

The main evaluation indexes of the freeze-drying protective agent investigation are as follows: the ERG and GEF entrapment efficiency changes little before and after freeze-drying; the appearance is loose, there are no collapse and shrinkage, and the color is uniform; the particle size changes little before and after freeze-drying; the freeze-dried powder is dissolved completely after rehydration.

3.1 Screening of Single Freeze-Drying Protective Agent

In the test, the ratio of carbohydrate to lipid was set to 6:1 (namely, the use amount of the freeze-drying protective agent was 294 mg), and freeze-drying was performed by the above freeze-drying process. The results are shown in FIG. 19. The test results show that the mannitol has good formability, and the appearance is full after freeze-drying, while the protective effect of sucrose and glucose on the liposome is better than that of lactose, and the entrapment efficiency of liposome is higher after redissolution. However, as a protective agent, glucose has a slightly high PDI value obtained by measuring the particle size after redissolution and poor dispersibility. Therefore, it is considered to use mannitol as a proppant so that the freeze-dried product has a good appearance, and the mannitol is further combined with sucrose for screening.

3.2 Determination of the Use Amount and Combined Ratio of Freeze-Drying Protective Agents In the experiment, nine groups of tests were designed by changing the ratio of carbohydrate to lipid and the ratio of sucrose to mannitol. The specific test is shown in FIG. 20. The appearance, the rehydration time, the average particle size, and the ERG and GEF entrapment efficiency of the sample before and after freeze-drying were used as selection indexes to investigate the protective effect thereof on the freeze-dried product. The test results are shown in FIG. 21. The results show that the appearances of the freeze-dried powder in Groups 1, 2, 4, and 7 are intact and loose, uniform and full, but the GEF entrapment efficiency of Group 1 is lower than that of the other three groups. It is speculated that the use amount of mannitol is more than that of sucrose, resulting in serious GEF leakage. Therefore, Groups 2, 4, and 7 were finally selected for the verification test, and the test was repeated 3 times.

3.3 Verification Test

The RGD/R8-ERG/GEF-LIP sample was prepared, and Groups 2, 4, and 7 in Tables 3-6 were selected for the verification test. The results are shown in FIG. 22. The results show that the appearance of each group is intact and loose, and uniform and full, wherein in Group 2, the rehydration time is 15 s, the shortest, the average particle size is $137.0\pm1.3$ nm, PDI is $0.210\pm0.003$, the ERG entrapment efficiency is $94.29\pm1.04\%$, and the GEF entrapment efficiency is $80.50\pm0.98\%$. In Group 4, the average particle size is $146.5\pm1.5$ nm, PDI is $0.214\pm0.008$, the ERG entrapment efficiency is $89.68\pm6.87\%$, and the GEF entrapment efficiency is 75.07±0.85%. In Group 7, the average particle size is 158.2±1.1 nm, PDI is 0.263±0.014, the ERG entrapment efficiency is 72.65±5.66%, and the GEF entrapment efficiency is 74.69±1.08%. In summary, Group 2 was selected as the final freeze-drying prescription and process. Through the above freeze-drying process and prescription investigation, the final freeze-drying process was determined as follows: the rapid freezing method was used, including: placing the sample at the cold trap in the equipment for 4 h, transferring to the upper layer to freeze-dry for 48 h (freeze-drying procedure: −20 to −10° C., 15 h; −10 to −0° C., 15 h; 0 to 10° C., 15 h; 10 to 20° C., 15 h; and 20 to 30° C., 12 h). The prescription of the freeze-drying protective agent was as follows: each liposome freeze-dried powder (5 mL) contained 245 mg of sucrose and 245 mg of mannitol (the ratio of carbohydrate to lipid ratio was 10:1, and the mass ratio of sucrose to mannitol was 1:1).

Figure 50:
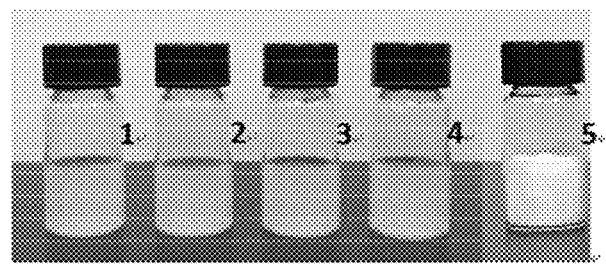
FIG. 50 shows the appearance of each liposome.

(IV) Quality Evaluation of RGD/R8-ERG/GEF-LIP Freeze-Dried Powder 1 Morphological observation 1.1 Appearance Morphology The RGD-ERG/GEF-LIP solution, R8-ERG/GEF-LIP solution, RGD/R8-ERG/GEF-LIP solution and RGD/R8-ERG/GEF-LIP freeze-dried powder after redissolution are all milky white and uniform in color. The RGD/R8-ERG/GEF-LIP freeze-dried powder is intact and loose, uniform and full in appearance, as shown in FIG. 50.

1.2 Microscopic Morphology (Observing Liposomes by Transmission Electron Microscope)

Figure 51:
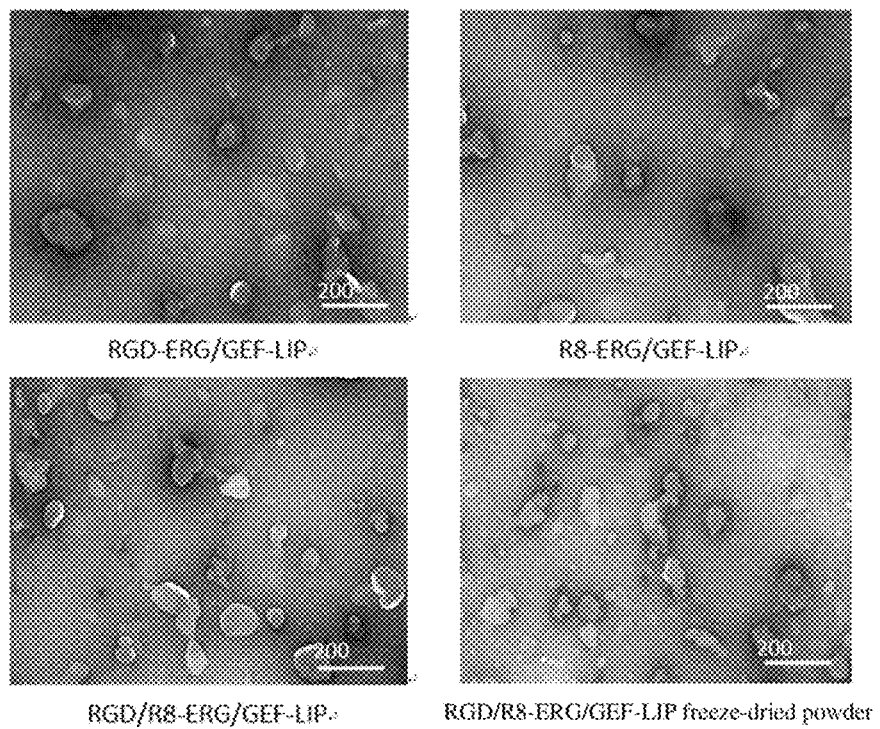
FIG. 51 shows a transmission electron micrograph of each liposome.

Samples were prepared by negative staining. At room temperature, the RGD-ERG/GEF-LIP, R8-ERG/GEF-LIP, RGD/R8-ERG/GEF-LIP, and RGD/R8-ERG/GEF-LIP freeze-dried powder samples were taken, and dropped onto a special copper mesh of an electron microscope, excess samples were blotted up with filter paper, and the samples were kept stand for 1 min, and then negatively stained with 1% phosphotungstic acid, and after keeping stand for 30 s, the excess staining solution on the copper mesh was sucked up by filter paper, and then the samples were naturally dried and observed and photographed by the electron microscopy. The transmission electron microscopy results show that the liposomes were round in morphology and uniform in particle size distribution (FIG. 51).

2 Particle Size and Distribution Thereof

Figure 52:
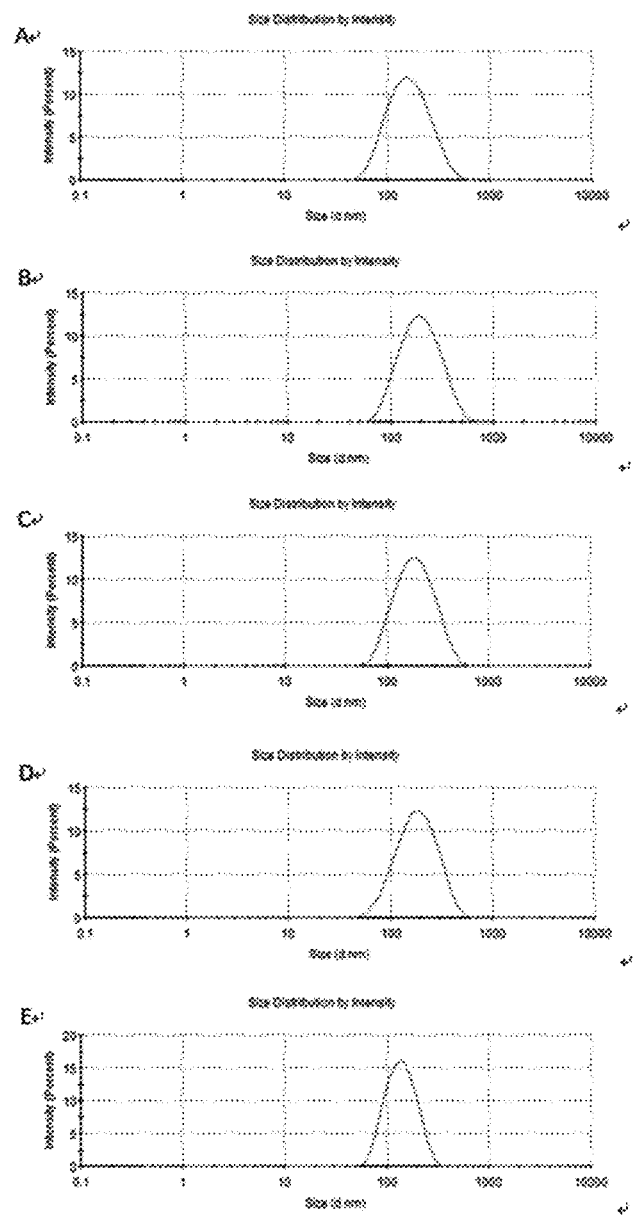
FIG. 52 shows a particle size distribution of each liposome.

At room temperature, ERG/GEF-LIP, RGD-ERG/GEF-LIP, R8-ERG/GEF-LIP, RGD/R8-ERG/GEF-LIP, and RGD/R8-ERG/GEF-LIP freeze-dried powder samples were taken, diluted 20 times with pure water and then injected into a sample cell, and the average particle size and the distribution thereof were measured by a laser particle size analyzer. The results are shown in FIG. 52. The results show that the average particle size of ERG/GEF-LIP is 142.8±2.8 nm, the polydispersity index PDI is 0.194±0.021, and less than 0.3; the average particle size of RGD-ERG/GEF-LIP is 147.0±0.7 nm, PDI is 0.166±0.018, and less than 0.3; the average particle size of R8-ERG/GEF-LIP is 148.5±2.5 nm, PDI is 0.184±0.021, and less than 0.3; the average particle size of RGD/R8-ERG/GEF-LIP is 149.6±1.9 nm. PDI is 0.191±0.027, and less than 0.3; and the average particle size of RGD/R8-ERG/GEF-LIP freeze-dried powder after redissolution is 132.8±1.2 nm, PDI is 0.181±0.012, and less than 0.3. It can be seen that the particle size distribution of each liposome is more centralized.

3 Measurement of Zeta Potential

Figure 53:
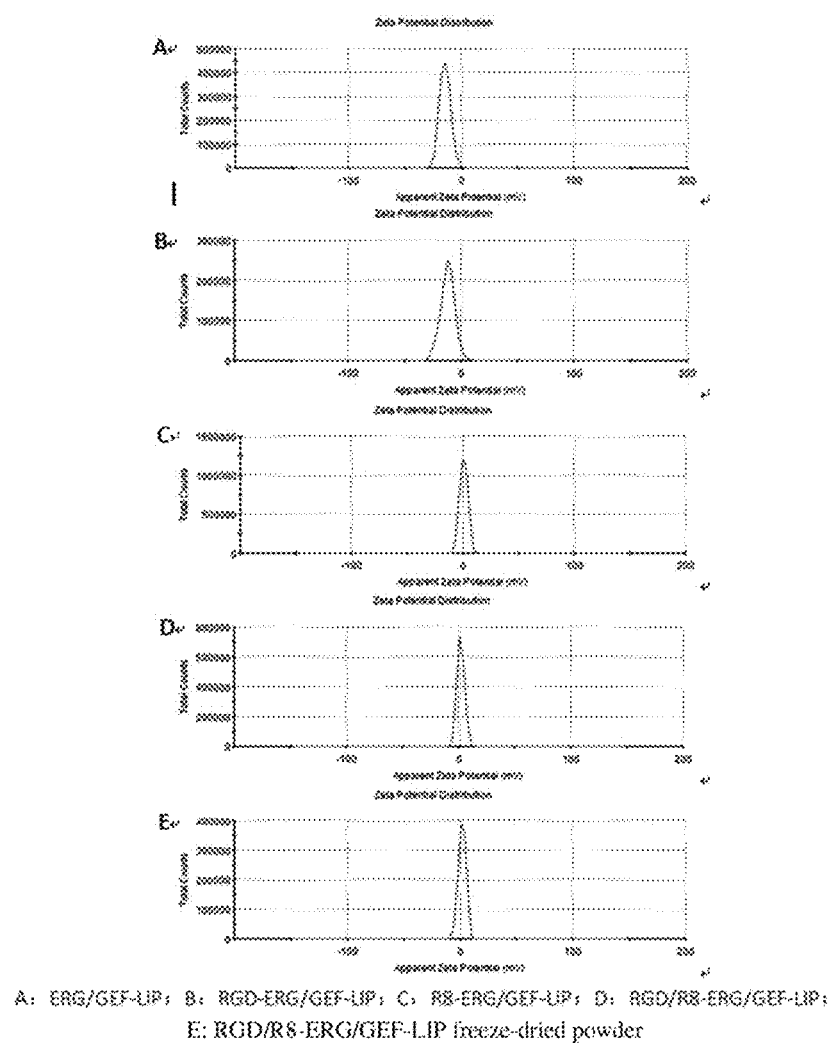
FIG. 53 shows a Zeta potential of each liposome.

At room temperature, the ERG/GEF-LIP, RGD-ERG/GEF-LIP, R8-ERG/GEF-LIP, RGD/R8-ERG/GEF-LIP, and RGD/R8-ERG/GEF-LIP freeze-dried powder samples were taken, and diluted 20 times with pure water, and the potential was measured by a Zeta potential meter, and the results are shown in FIG. 53. The results show that the Zeta potential of ERG/GEF-LIP is −18.9±0.6 mV, the Zeta potential of RGD-ERG/GEF-LIP is −12.2±0.5 mV, the Zeta potential of R8-ERG/GEF-LIP is 0.769±0.037 mV, the Zeta potential of RGD/R8-ERG/GEF-LIP is 1.87±0.09 mV, and the Zeta potential of RGD/R8-ERG/GEF-LIP freeze-dried powder after redissolution is 5.61±0.22 mV.

Figure 54:
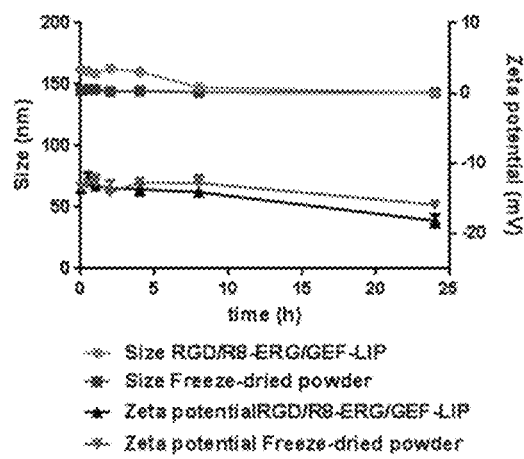
FIG. 54 shows investigation of serum stability of RGD/R8-ERG/GEF-LIP and the freeze-dried powder thereof.

4 Serological Stability Investigation 1 mL of RGD/R8-ERG/GEF-LIP and 1 mL of the freeze-dried powder thereof were taken, and mixed with filtered fetal bovine serum according to a volume ratio of 1:1, 100 μL of a mixture was respectively taken at 0, 0.5, 1, 2, 4, 8 and 24 h and diluted 10 times with pure water, and the particle size and Zeta potential were measured by a laser particle size analyzer/zeta potential analyzer, and the results are shown in FIG. 23 and FIG. 54. The experimental results show that RGD/R8-ERG/GEF-LIP has a particle size of about 160 nm in the first 4 h, and the particle size drops to 143.1 nm at 24 h. However, the RGD/R8-ERG/GEF-LIP freeze-dried powder after redissolution has a particle size stable at about 140 nm within 24 h, indicating that it has good serum stability.

5 Entrapment Efficiency and Drug Loading Capacity

Three batches of RGD/R8-ERG/GEF-LIP freeze-dried powder samples were taken, wherein the average entrapment efficiency of GEF was 80.50±0.98%, and the drug loading capacity was 4.67±0.17%. The average entrapment efficiency of ERG was 94.29±1.04%, and the drug loading capacity was 3.59±0.41%.

6 Release Rate

In the experiment, the in vitro release of GEF drug under different pH conditions was investigated. 4 mL of the RGD/R8-ERG/GEF-LIP freeze-dried powder and 4 mL of the GEF citric acid solution were accurately absorbed. For specific operation, please refer to "5.7 Release Rate" in Part II in details.

Figure 55:
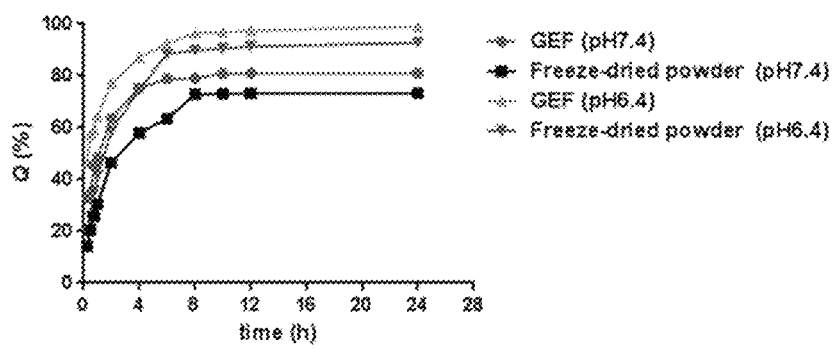
FIG. 55 shows cumulative release rates of GEF and the RGD/R8-ERG/GEF-LIP freeze-dried powder in different pH release media.

The results from FIG. 55 show that the in vitro release of GEF has significant pH dependence. In the pH 7.4 40% methanol-containing phosphate buffer, the cumulative release percentage of a GEF raw medicine within 24 h was 81.10%, and the cumulative release percentage of RGD/R8-ERG/GEF-LIP freeze-dried powder was 73.34%. In the pH 6.4 40% methanol-containing phosphate buffer, the cumulative release percentage of the GEF raw medicine within 24 h was 99.12%, and the GEF raw medicine was almost completely released. The cumulative release percentage of RGD/R8-ERG/GEF-LIP freeze-dried powder within 0.5 h was 25.60%<40%, and the cumulative release percentage of RGD/R8-ERG/GEF-LIP freeze-dried powder within 6 h was 88.55%>80%, and the cumulative release percentage of RGD/R8-ERG/GEF-LIP freeze-dried powder was 92.80% until 24 h. The requirements for the liposome burst effect in the *Chinese Pharmacopoeia* 2015 edition are as follows: the release amount within 0.5 h at the beginning should be ≤40% [49], and the cumulative release percentage within 24 h exceeds 80%. The RGD/R8-ERG/GEF-LIP freeze-dried powder meets the requirements in the condition that the pH 6.4 40% methanol-containing phosphate buffer served as the release medium. Double-target drug-loaded liposomes were more readily released in a weakly acidic environment, which will be favorable for the liposomes to selectively release the contents in the tumor acidic environment, and play a dual targeting role.

In this paper, the cumulative release percentages of the GEF solution and RGD/R8-ERG/GEF-LIP freeze-dried powder (first 4 h) were respectively fitted according to the zero-order, first-order and Higuchi equations. The model formula is shown in FIG. 24, and the fitting results and correlation coefficients are shown in FIG. 25.

FIG. 25 shows fitting results and correlation coefficients of cumulative release rates of drugs. The fitting results show that in the pH 7.4 release medium, the in vitro release of the GEF citric acid solution and the RGD/R8-ERG/GEF-LIP freeze-dried powder is more in line with the Higuchi model. In the pH 6.4 release medium, the in vitro release of the GEF citric acid solution and the RGD/R8-ERG/GEF-LIP freeze-dried powder is more in line with the first-order model.

7 Inhibition Test on Proliferation of Drug-Resistant Cells In Vitro

Figure 56:
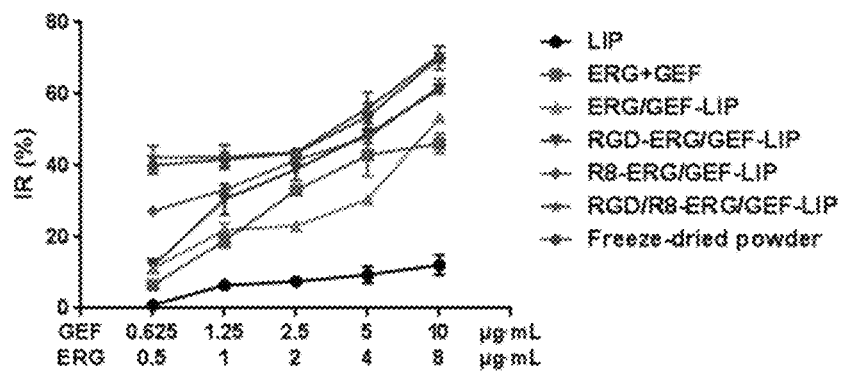
FIG. 56 shows the 24 hMTT test results of each liposome.

The PC-9/GR cells were cultured in vitro, and administrated with the blank liposome (LIP), ERG-LIP, ERG/GEF-LIP, RGD-ERG/GEF-LIP, R8-ERG/GEF-LIP, RGD/R8-ERG/GEF-LIP, and RGD/R8-ERG/GEF-LIP freeze-dried powder to stimulate for 24 h, and then the cell proliferation inhibitory rates after administrating different concentrations of drugs were measured. For the specific operation, please refer to "(IV) Research on inhibitory effects of ERG combined with GEF on proliferation of A549 and PC-9 cells (MTT test)" in Part I in details. In the experiment, measurement was performed in parallel three times, and the results are shown in FIG. 56. The results show that when the drug acts for 24 h, the inhibitory rate at each concentration in the LIP group is less than 15%, indicating that the excipient has no inhibitory effect on the drug-resistant cells within this concentration range. At the same administration concentration, the inhibitory rate of the double-target modified liposome was significantly higher than that of the single-target modified liposome ($P<0.01$), and the inhibitory rates of RGD/R8-ERG/GEF-LIP and RGD/R8-ERG/GEF-LIP freeze-dried powder groups were similar, and there was no significant difference ($P>0.05$), indicating that when the double-target liposome is prepared into a freeze-dried powder form, the inhibitory effect on proliferation of PC-9/GR cells cannot be decreased.

8 In vitro Drug-Resistant Cell Uptake Test

Figure 57:
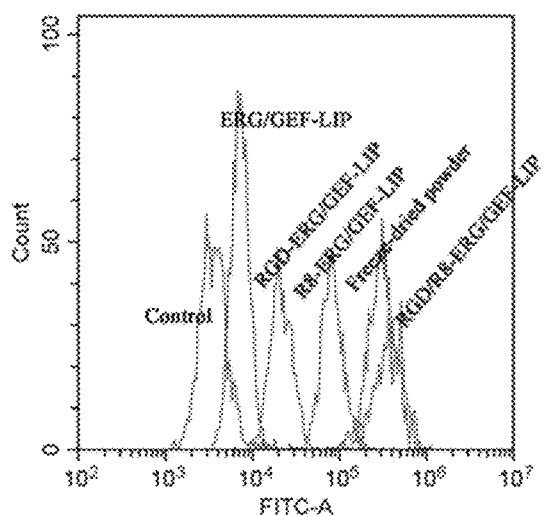
FIG. 57 shows the fluorescence uptake intensity of each fluorescent drug-loaded liposome.

The FITC methanol solution was subjected to rotary evaporation together with SPC, Chole and ERG to form a film, and the concentration of FITC in the prepared liposome was 137.5 $\mu L^{-1}$. The prepared FITC-labeled ERG/GEF-LIP, RGD-ERG/GEF-LIP, R8-ERG/GEF-LIP, and RGD/R8-ERG/GEF-LIP freeze-dried powder were quantitatively diluted with the complete 1640 medium until the final concentration of FITC was 25 $\mu g \cdot mL^{-1}$. For the specific operation, please refer to "5.10 In vitro drug-resistant cell uptake test of ERG/GEF-LIP" in Part II in details. In the experiment, measurement was performed in parallel 3 times, and the results are shown in FIG. 57. The results show that the sequence of fluorescence uptake intensity is as follows: RGD/R8-ERG/GEF-LIP≈RGD/R8-ERG/GEF-LIP freeze-dried powder>R8-ERG/GEF-LIP>RGD-ERG/GEF-LIP>ERG/GEF-LIP, indicating that the double-target liposome has better fluorescence uptake effects than the single-target liposome, and when RGD/R8-ERG/GEF-LIP was prepared into the freeze-dried powder, the fluorescence uptake effect on PC-9/GR cells was not decreased.

9 In Vitro Drug-Resistant Cell Apoptosis Test

Figure 58:
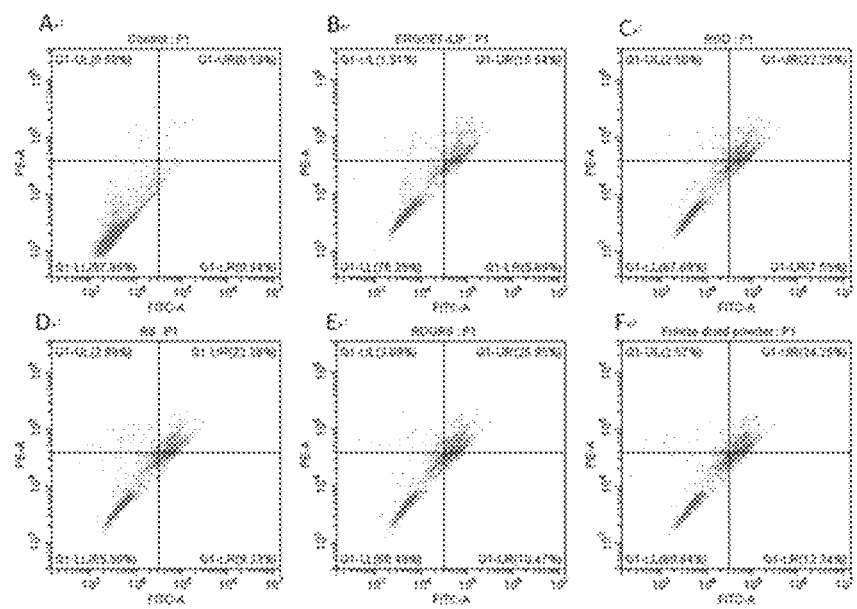
FIG. 58 shows a flow diagram of apoptosis of PC-9/GR cells.

The PC-9/GR cells were cultured in vitro, and administrated with ERG/GEF-LIP, RGD-ERG/GEF-LIP, R8-ERG/GEF-LIP, RGD/R8-ERG/GEF-LIP, and RGD/R8-ERG/GEF-LIP freeze-dried powder groups to stimulate for 24 h, and the specific operation can refer to "1 Measurement of apoptotic rate" in Part I in details. In the experiment, measurement was performed in parallel 3 times, and the test results are shown in FIG. 58 and FIG. 26. The results show that the apoptotic rate of each administration group is significantly higher than that of the blank control group ($P<0.01$). Among them, the apoptotic rates of RGD/R8-ERG/GEF-LIP and RGD/R8-ERG/GEF-LIP freeze-dried powder groups were significantly different from that of the single-target modified liposome ($P<0.01$). There was no significant difference in apoptotic rate between RGD/R8-ERG/GEF-LIP and RGD/R8-ERG/GEF-LIP freeze-dried powder groups ($P>0.05$), indicating that when RGD/R8-ERG/GEF-LIP is prepared into freeze-dried powder, the apoptosis effect on PC-9/GR cells is not decreased.

III Analysis and Discussions

In the test of this part, based on the test in Part II, the RGD cyclic peptide and the R8 peptide were linked to DSPE via PEG, the modifying peptide was directly modified on the surface of the liposome as a phospholipid material to prevent it from detaching from the surface of the liposome after entering the human circulatory system, thereby increasing the stability of the co-modified liposome. Considering that the RGD peptide can specifically bind to the integrin receptor on the cell surface, and this receptor is highly expressed on the surfaces of activated endothelial cells and tumor cells [60-63], thus increasing the modification of the transmembrane peptide R8 peptide can increase the endocytosis probability of the liposome. Considering that the stability problem of the liposome itself, the freeze-drying process and prescription of RGD/R8-ERG/GEF-LIP were investigated by taking the appearance, particle size, rehydration time, and entrapment efficiency of the freeze-dried powder as evaluation indexes in this chapter.

It is found by referring to the pertinent literatures that the crystallization of the liposome suspension belongs to homogeneous nucleation, that is, the temperature drop causes the random thermal fluctuation in a liquid phase, so that the molecules therein are aggregated into the nucleus. By using the quick-freezing method, the nucleation probability was high, and more crystal nuclei were formed in a unit volume, thereby forming a fine ice crystal structure, and the finally obtained product was intact in appearance, loose and easy to dissolve. On the contrary, the surface concentrated layer formed by the slow-freezing method was thicker, and prevented the escape of water vapor, so that the freeze-drying time was prolonged, the holes left after the sample was sublimated were large, and the obtained freeze-dried product was easily collapsed [64]. The theory was consistent with the results obtained in this experiment, so the final freeze-drying process was determined as follows: the rapid freezing method was used, including: placing the sample at the cold trap in the equipment for 4 h, transferring to the upper layer to freeze-dry for 48 h (freeze-drying procedure: −20 to −10° C., 15 h; −10 to −0° C., 15 h; 0 to 10° C., 15 h; 10 to 20° C., 15 h; and 20 to 30° C., 12 h). The prescription of the freeze-drying protective agent was as follows: each lipsome freeze-dried powder (5 mL) contains 245 mg of sucrose and 245 mg of mannitol (the ratio of carbohydrate to lipid ratio is 10:1, and the mass ratio of sucrose to mannitol is 1:1). In the freeze-dried product, the average entrapment efficiency of GEF was 80.50±0.98%, which was slightly decreased. The serological stability test shows that the RGD/R8-ERG/GEF-LIP freeze-dried powder has good serum stability. The proliferation inhibition test, uptake test and apoptosis test of in vitro drug-resistant cells confirm that the effect of RGD/R8-ERG/GEF-LIP freeze-dried powder basically had no difference with that before freeze-drying.

IV. Conclusions

In this part, the RGD/R8-ERG/GEF-LIP active drug-loaded liposome delivery system was successfully constructed. In order to save the experimental cost, the ERG/GEF-LIP was used to investigate the freeze-drying process and prescription, and the best prescription and process were screened out and applied to RGD/R8-ERG/GEF-LIP for verification. The in vitro test results of RGD/R8-ERG/GEF-LIP freeze-dried powder confirm that it has stronger tumor cell proliferation inhibitory effects, fluorescence uptake intensity and good apoptotic rate.

Tumor Inhibitory Effect and In Vivo Targeting Research of RGD Cyclic Peptide/R8 Peptide Modified ERG-GEF Combined Compound Liposome Freeze-Dried Powder in Nude Mice In this part, BABL/C nude mice were selected, and PC-9/GR cells were inoculated in the dorsal sides [65-66]. When the tumor grew to a volume of 200 mm$^3$, the tail vein was administered by injection for two weeks. Preliminary pharmacodynamic research (i.e., research on in vivo tumor inhibitory effects) was conducted by taking the body mass of the nude mouse, tumor volume change, tumor weight, tumor inhibitory rate, spleen index, IL-2, TGF-β1, TIMPs, and TNF-α levels in serum, spleen and tumor tissue pathological characteristics as indexes. A small animal in vivo fluorescence imaging system [67-70] was used to observe the in vivo distribution of liposomes at different time points after administration, and the tumor, heart, liver, spleen, lung and kidney were taken by dissection the next day, and the fluorescence distribution of in vitro tissues was observed.

(1) Preliminary Pharmacodynamic Test

1 Animal Grouping

A PC-9/GR lung cancer cell line was digested from a culture flask, and then resuspended in 0.9% normal saline, and the cell concentration was adjusted to $2.5 \times 10^7 \cdot mL^{-1}$ and the cell was inoculated into the left axilla of BABL/C nude mouse. Each nude mouse was inoculated with 0.2 mL of a cell suspension. When the tumor grew to 200 mm$^3$, the nude mice were randomly divided into a normal control group, a model control group, a positive drug group, ERG/GEF-LIP, RGD/R8-ERG/GEF-LIP, and RGD/R8-ERG/GEF-LIP freeze-dried powder groups, and there were 5 mice in each group.

2 Administration Method

The nude mice in each group were administered by tail vein injection. The normal control group and the model control group were administrated with normal saline, 0.4 mL per mouse; the positive drug group was administrated with the GEF solution with the same concentration as the liposome, 0.4 mL per mouse; ERG/GEF-LIP, RGD/R8-ERG/GEF-LIP, and RGD/R8-ERG/GEF-LIP groups were the same, 0.4 mL per mouse; injection was performed every other day, with a total of 7 times.

3 Observation of Indexes 3.1 Body Mass, Tumor Volume Change and Tumor Inhibitory Rate of Nude Mice in Each Group After starting administration, the body mass of the nude mouse was regularly measured once, and the longest and shortest diameters of the tumor were measured with a vernier caliper to calculate the volume of the tumor. After consecutively administrating 7 times, the tumor volume of each group was measured and the tumor inhibitory rate of each administration group was calculated.

Tumor volume (mm$^3$)=½×Long diameter (mm)× Short diameter (mm)$^2$

Tumor inhibitory rate (%)=(Average tumor weight of model control group (mg)—Average tumor weight of administration group (mg))/Average tumor weight of model control group (mg)×100%

3.2 Spleen Index of Nude Mice in Each Group

The spleens of nude mice were completely taken out and weighed, and the spleen index was calculated.

Spleen index=Spleen weight (mg)/Body mass (g)×10

3.3 Measurement of IL-2, TGF-β1, TIMPs, and TNF-α levels in serum of nude mice

After the body mass and tumor diameter of the nude mouse were measured, the eyeballs of the nude mouse were enucleated and blood was taken and placed in an anticoagulation tube, and the nude mouse was rapidly killed by cervical dislocation. The serum was taken by centrifuging at 4000 rpm·min$^{-1}$ for 15 min, and the contents of IL-2, TGF-β1, TIMPs and TNF-α in each group were measured by the operation in strict accordance with the instructions of the kit.

3.4 Pathological Changes of Tumor Tissue, Spleen and Lung of Nude Mice in Each Group HE staining was used, the tumor tissue, spleen and lung were taken out and fixed in formalin, and samples were taken and made into sections for pathological observation.

3.5 Statistical Processing

The experimental data was expressed as mean±standard deviation (x±s), and statistically processed by SPSS 17.0 statistical software, one-way analysis of variance was used, and t test was used for comparison between the two groups. $P<0.05$ shows that there is a significant difference, and $P<0.01$ shows that there is a highly significant difference.

Figure 59:
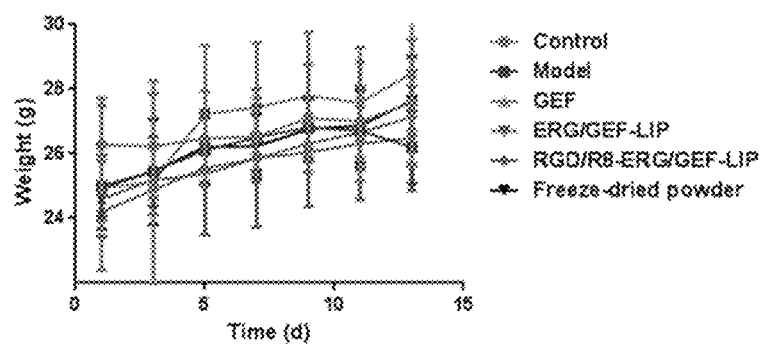
FIG. 59 shows changes in body mass of nude mice in each group.

4 Experimental Results 4.1 Body Mass, Tumor Volume and Tumor Inhibitory Rate of Nude Mice in Each Group 4.1.1 Change in Body Mass of Nude Mice After starting administration, the body mass of the nude mouse was measured on the 1st, 3rd, 5th, 9th, 11th, 13th, and 15th days. The body mass change curves of nude mice in each group are shown in FIG. 27 and FIG. 59. The results show that the body masses of nude mice in each group are not decreased during administration, and all show a steady upward trend. The body mass of each group on the 15th day was significantly higher than that of the 1st day ($P<0.05$ and $P<0.01$), indicating that the drug has little effect on the body masses of nude mice before and after administrating in each group. On the 15th day, there was no difference in body mass among the groups by one-way analysis of variance ($P>0.05$).

4.1.2 Tumor Volume Change

Figure 60:
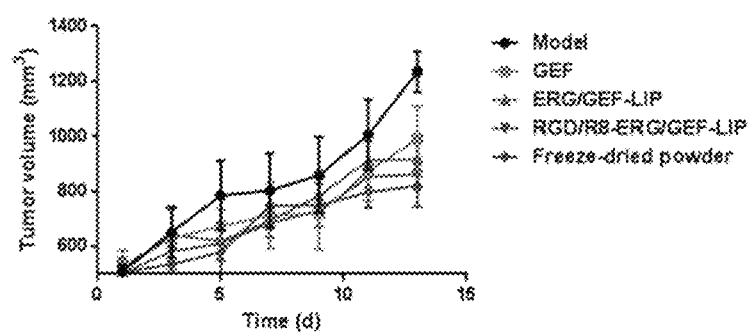
FIG. 60 shows a tumor growth curve of nude mice in each group.

After starting administration, the long and short diameters of the tumor of the nude mouse were measured on the 1st, 3rd, 5th, 9th, 11th, 13th, and 15th days, and the tumor volume was calculated. The measurement results are shown in FIG. 28 and FIG. 60. The results show that the xenograft in each group shows an increase in volume and local nodular growth after administration. In the positive drug group, the tumor volume shows a rapid growth trend after the 9th day of administration. It is speculated that for PC-9/GR drug-resistant xenografts, the gefitinib raw medicine may inhibit the increase of tumor volume to a certain extent in the first 9 days, but after 9 days, the gefitinib raw medicine may have certain drug resistance to the xenografts, which eventually leads to a rapid increase in tumor volume. The RGD/R8-ERG/GEF-LIP and RGD/R8-ERG/GEF-LIP freeze-dried powder groups showed minimal tumor volume changes after 15 days of administration. On the 15th day, compared with the model control group, the tumor volume of ERG/GEF- LIP was significantly decreased (P<0.05), and the tumor volumes of RGD/R8-ERG/GEF-LIP and RGD/R8-ERG/GEF-LIP freeze-dried power groups were significantly decreased (P<0.01).

4.1.3 Tumor Inhibitory Rates of Nude Mice in Each Group

It can be seen from the data in FIG. 29 that for PC-9/GR tumor-bearing nude mice, compared with the model control group, the average tumor weights of positive drug, ERG/GEF-LIP, RGD/R8-ERG/GEF-LIP, and RGD/R8-ERG/GEF-LIP freeze-dried powder groups had a highly significant difference (P<0.01), and the tumor inhibitory rates were 21.91%, 26.41%, 35.09%, and 33.58%, respectively. There was no significant difference in the average tumor weight between the RGD/R8-ERG/GEF-LIP and RGD/R8-ERG/GEF-LIP freeze-dried powder groups (P>0.05). It indicates that when RGD/R8-ERG/GEF-LIP is prepared into a freeze-dried powder form, the inhibitory effect of liposome on PC-9/GR lung cancer xenografts in nude mice cannot be affected.

4.2 Spleen Index of Nude Mice in Each Group

The data in FIG. 30 show that compared with the normal control group and the model control group, the spleen index of the positive drug group is decreased, and the difference is significant (P<0.05), indicating that the immunity of the nude mice is reduced to a certain extent under the action of the positive drug. Compared with the positive drug group, the spleen indexes of ERG/GEF-LIP, RGD/R8-ERG/GEF-LIP, and RGD/R8-ERG/GEF-LIP freeze-dried powder groups were increased (P<0.01, P<0.01, and P<0.05). Among them, the spleen index of the ERG/GEF-LIP group was abnormally increased. The reason may be that during the tail vein injection, the ERG/GEF-LIP drug is more irritating to nude mice, leading to the abnormal phenomenon of splenomegaly. There was no significant difference in spleen index among the blank control group, the model control group, RGD/R8-ERG/GEF-LIP and RGD/R8-ERG/GEF-LIP freeze-dried powder groups (P>0.05).

4.3 IL-2, TGF-β1, TIMPs, TNF-α Levels in Serum of Nude Mice

Figure 61:
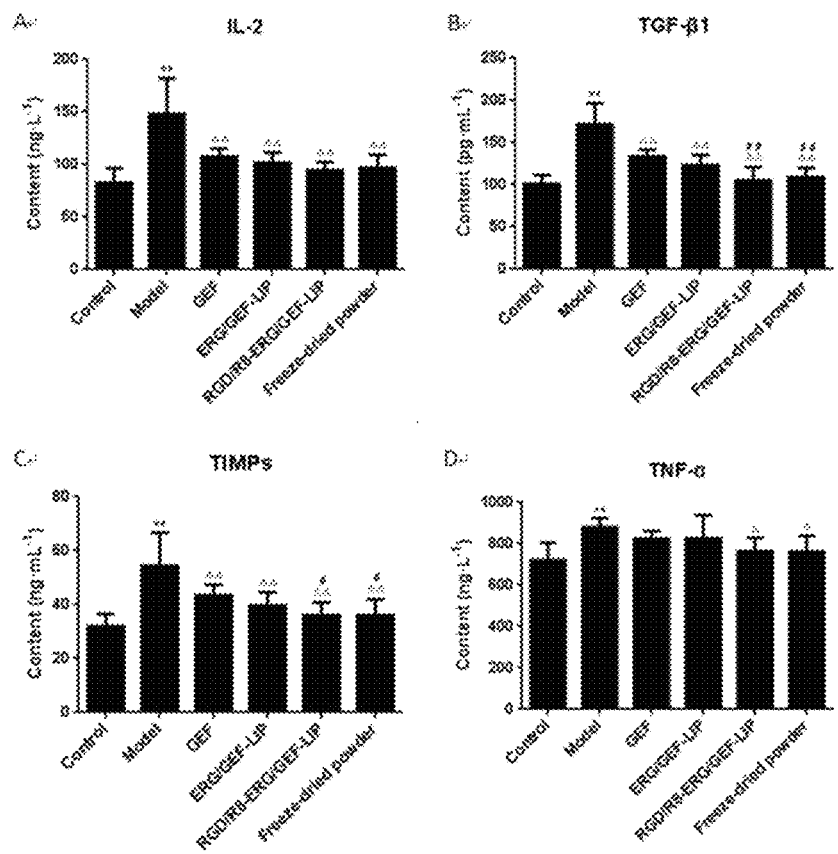
FIG. 61 shows the contents of IL-2, TGF-β1, TIMPsC and TNF-α in serum of nude mice in each group.

The results are shown in FIG. 31 and FIG. 61. Compared with the blank control group, the IL-2, TGF-β1, TIMPs and TNF-α levels in serum of the model control group were significantly increased (P<0.01). Compared with the model group, the IL-2, TGF-β1, and TIMPs levels in serum of each administration group were significantly decreased (P<0.01), and TNF-α levels in serum of the RGD/R8-ERG/GEF-LIP and RGD/R8-ERG/GEF-LIP freeze-dried powder groups were significantly decreased (P<0.05). Compared with the positive drug group, the TGF-⊖1 and TIMPs levels in serum of the RGD/R8-ERG/GEF-LIP and RGD/R8-ERG/GEF-LIP freeze-dried powder groups were significantly decreased (P<0.01). There was no significant difference in IL-2, TGF-β1, TIMPs, and TNF-α levels in serum between the RGD/R8-ERG/GEF-LIP and RGD/R8-ERG/GEF-LIP freeze-dried powder groups (P>0.05).

Figure 62:
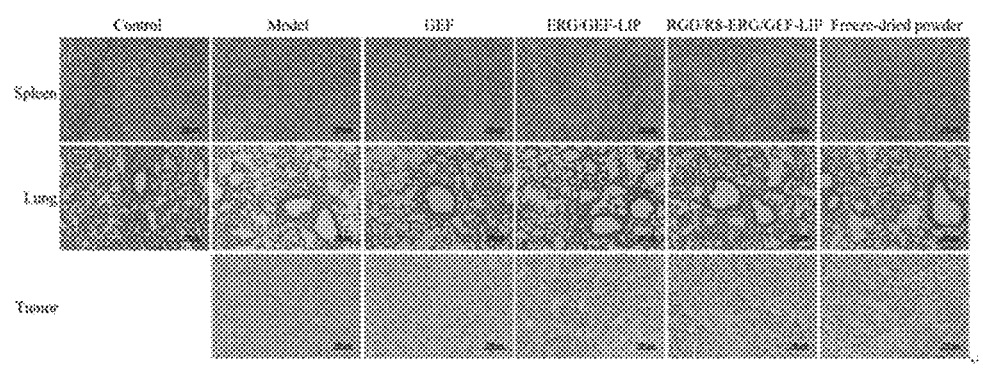
FIG. 62 shows the histopathological characteristics of nude mice in each group.

4.4 Pathological Characteristics of Tumor, Spleen and Lung Tissues of Nude Mice in Each Group The results are shown in FIG. 62. The spleen and lung tissues of each group had normal morphological characteristics, and there was no obvious pathological change, indicating that the drug has no toxicity to the spleen and lung. The tumor tissue in the model group was rich in cancer cells, and arranged closely, and had less intercellular substances and deep-dyed big nuclei. The number of tumor tissues in each administration group was reduced, the density was decreased, the cell shrinkage caused gaps, the nucleus was pyknotic and fragmented, and all of them had obvious cell necrosis and were separated. Regional necrosis occurred between tissues, and the area of light red cytoplasm was increased.

The nude mice with a body mass of approximately 25 g in the established PC-9/GR tumor-bearing nude mouse model were taken, and respectively injected with 0.2 mL of a DiR raw medicine, and DiR-coated RGD/R8-ERG/GEF-LIP and RGD/R8-ERG/GEF-LIP freeze-dried powder (DiR concentration: 7.5 μg·mL$^{-1}$) by tail vein injection, the nude mice were anesthetized with isoflurane at different time points, and placed in an in vivo imager to observe the distribution of liposome in vivo (Ex=748 nm, Em=780 nm, and exposure time: 2 s). After 24 h, after the last in vivo imaging was finished, the nude mice were killed, and the heart, liver, spleen, lung, kidney and tumor were taken out and placed in the in vivo imager to observe the distribution of liposome in the in vitro tissues. After the DiR raw medicine entered the nude mice, the fluorescence was not accumulated in the tumor site within 24 h, and the distribution of in vitro tissues showed that the fluorescence was mostly observed in the liver and spleen. In the real-time in vivo fluorescence imaging tests of RGD/R8-ERG/GEF-LIP and freeze-dried powder groups, fluorescence was observed to accumulate in the tumor site. It was also observed in the in vitro tissues that the fluorescence intensity of the freeze-dried powder group in the tumor site was slightly higher than that of the RGD/R8-ERG/GEF-LIP group. It is speculated that the particle size of freeze-dried powder is smaller than that of RGD/R8-ERG/GEF-LIP, which increases the probability of entering the tumor cells to a certain extent and increases the tumor targeting effect in vivo.

III Analysis and Discussions

Under the long-term stimulation of chronic inflammation, the tumors release many cytokines that promote its own growth, these cytokine-mediated signal pathways are involved in the malignant development of tumor cells, thus forming a tumor inflammation microenvironment, which is conducive to the occurrence and further development of tumors. IL-2 is a cellular inflammatory factor involved in immune regulation. When there is a tumor inflammation microenvironment in the body, IL-2 may be over-expressed [71-72]. TGF-β1 is a polypeptide enzyme growth inhibitory factor, and the over-expression of TGF-β1 leads to the breakage of balance, which can affect the normal function of tumor immune function, and make tumor cells escape immune system monitoring [73-74]. TIMPs are cytokines that inhibit the activity of matrix metalloproteinases (MMPs). During the occurrence and development process of tumors, MMPs are often over-expressed, leading to tumor invasion and metastasis and angiogenesis [75-76]. TNF-α is a cytokine that can promote tumor growth. Chronic long-term secretion of TNF-α provides conditions for tumor growth and progression. The increase in serum TNF-α in patients with malignant tumor may be related to the tumor infiltrating cells undergoing tumor antigen stimulation during the metastasis process of tumor cells, resulting in increase in produced TNF-α[77-79]. These four cytokines play an important role in inhibiting tumor growth and other aspects, and are closely related to the occurrence and development of malignant tumors. The expression levels thereof can indirectly reflect the body immune function status and tumor progression.

In the test of this part, preliminary pharmacodynamic research was conducted by taking the tumor volume change, tumor inhibitory rate, spleen index, IL-2, TGF-β1, TIMPs and TNF-α levels in serum, spleen and tumor tissue pathological characteristics of the nude mice as indexes. The preliminary pharmacodynamic research shows that the drug has little effect on the body mass of nude mouse during the administration, and the tumor volume growth rate of the administration group was smaller than that of the model group. The tumor inhibitory rates of the positive drug, ERG/GEF-LIP, RGD/R8-ERG/GEF-LIP, and RGD/R8-ERG/GEF-LIP freeze-dried powder groups were 21.91%, 26.41%, 35.09%, and 33.58%, respectively. The spleen index of the positive drug group was decreased to a certain extent compared with the model group (P<0.05), suggesting that the raw medicine has side effects of reducing immunity. It can be seen from the IL-2, TGF-β1, TIMPs and TNF-α levels in serum that the indexes of components of the model group were all higher than those of the blank control group, indicating that the model is successfully established. After the administration, the indexes of components were decreased to different extents, wherein the effects of the RGD/R8-ERG/GEF-LIP and RGD/R8-ERG/GEF-LIP freeze-dried powder groups were the best. The results of pathological sections show that the necrotic area of the tumor tissue of the administration group was increased, and the spleen and lung tissues have normal morphological characteristics.

The effective technology was used to label and trace the targeting effect of an active targeting preparation, which will facilitate the animal experiment research and clinical application. The fluorochrome DiR is stable in property, has no toxicity, and has a long tracing period, and gradually becomes a commonly used dye for tracing. The in vivo fluorescence imaging test shows that the fluorescence of the drug-loaded liposome is accumulated in the tumor site, confirming that it has certain targeting ability. The tumor tissues and other tissues of the nude mouse were taken in vitro and it was found that the fluorescence of the drug was accumulated in the liver, spleen and tumor tissues. On the other hand, it proved that the drug-loaded liposome had certain targeting ability.

IV. Conclusions

In this part, the related in vivo research was conducted, wherein the preliminary pharmacodynamic test indicates that the RGD/R8-ERG/GEF-LIP freeze-dried powder has no significant toxic and side effects on nude mice and does not cause adverse effects such as mental disorders and weight loss in nude mice during administration, and the in vivo tumor inhibitory effects of RGD/R8-ERG/GEF-LIP freeze-dried powder and RGD/R8-ERG/GEF-LIP have little difference. It indicates that when the RGD/R8-ERG/GEF-LIP is prepared into a freeze-dried powder form, the inhibitory effect of liposome on PC-9/GR lung cancer xenografts in nude mice cannot be affected. The targeting test also confirms that the prepared drug-loaded liposome has certain targeting ability.

What is claimed:

1. A process comprising treating non-small cell lung cancer with a drug having a therapeutic mechanism, the drug comprising ergosterol combined with gefitinib.

2. The process according to claim 1, wherein the therapeutic mechanism is based on the synergistic inhibitory effect of ergosterol combined with gefitinib on PC-9 cells and/or A549 cells.

3. The process according to claim 1, wherein the therapeutic mechanism is based on the synergistic apoptosis-inducing effect of ergosterol combined with gefitinib on PC-9 cells and/or A549 cells.

4. The process according to claim 2, wherein the synergistic inhibitory effect is based on the combination of ergosterol and gefitinib to increase G0/G1 phase arrest and reduce the S phase fraction of cell cycle on A549 cells and/or PC-9 cells.

5. The process according to claim 3, wherein the synergistic apoptosis-inducing effect is based on the combination of ergosterol and gefitinib to inhibit expression of an EGFR signal pathway on A549 cells and/or PC-9 cells, and the EGFR signal pathway is a P13K/AKT/mTOR signal pathway.

6. The process according to claim 4, wherein the ergosterol has a drug concentration of 20 to 40 μM, and the gefitinib has a drug concentration of 2.5 to 5 μM.

7. The process according to claim 4, wherein the ergosterol has a drug concentration of 20 to 80 μM, and the gefitinib has a drug concentration of 5 to 40 μM.

8. A preparation method of a freeze-dried powder of the ergosterol-gefitinib combined compound liposome, comprising: adding a freeze-drying protective agent to a pre-prepared RGD/R8-ERG/GEF-LIP liposome suspension by an external addition method; and then preparing the freeze-dried powder of the compound liposome by a freeze-drying method; the RGD/R8-ERG/GEF-LIP liposome suspension being prepared by the following method, comprising: firstly preparing ERG/GEF-LIP, and then preparing the RGD/R8-ERG/GEF-LIP liposome suspension by a post-insertion method.

9. The preparation method of the freeze-dried powder of the ergosterol-gefitinib combined compound liposome according to claim 8, wherein the freeze-drying method is a quick-freezing method comprising: pre-lowering the temperature of a cold trap portion in equipment to a minimum temperature, and then placing a sample in the cold trap.

10. The preparation method of the freeze-dried powder of the ergosterol-gefitinib combined compound liposome according to claim 8, wherein the freeze-drying time of the freeze-drying method is 48 h.

11. The preparation method of the freeze-dried powder of the ergosterol-gefitinib combined compound liposome according to claim 8, wherein the freeze-drying protective agent is a combination of sucrose and mannitol, the ratio of carbohydrate to lipid is 10:1, and the mass ratio of sucrose to mannitol is 1:1.

12. The preparation method of the freeze-dried powder of the ergosterol-gefitinib combined compound liposome according to claim 8, wherein the preparation method of the RGD/R8-ERG/GEF-LIP liposome suspension specifically comprises: weighing SPC, Chole and RGD peptide according to a molar ratio of 5:1:0.07 to prepare R8-ERG/GEF-LIP; and weighing SPC, Chole, RGD peptide and RGD peptide according to a molar ratio of 5:1:0.07:0.07 to prepare the RGD/R8-ERG/GEF-LIP liposome suspension.

13. The preparation method of the freeze-dried powder of the ergosterol-gefitinib combined compound liposome according to claim 8, wherein the quick-freezing method is used, comprising: placing the sample at the cold trap in the equipment for 4 h, transferring to the upper layer for freeze-drying, and the freeze-drying procedure being as follows: −20 to −10° C., 15 h; −10 to 0° C., 15 h; 0 to 10° C., 15 h; 10 to 20° C., 15 h; and 20 to 30° C., 12 h.

* * * * *